(12) United States Patent
Goldfine et al.

(10) Patent No.: US 7,876,094 B2
(45) Date of Patent: Jan. 25, 2011

(54) MAGNETIC FIELD CHARACTERIZATION OF STRESSES AND PROPERTIES IN MATERIALS

(75) Inventors: Neil J. Goldfine, Newton, MA (US); Ian C. Shay, Cambridge, MA (US); Darrell E. Schlicker, Watertown, MA (US); Andrew P. Washabaugh, Chula Vista, CA (US); David C. Grundy, Reading, MA (US); Robert J. Lyons, Boston, MA (US); Vladimir A. Zilberstein, Chestnut Hill, MA (US); Vladimir Tsukernik, West Roxbury, MA (US)

(73) Assignee: JENTEK Sensors, Inc., Waltham, MA (US)

( * ) Notice: Subject to any disclaimer, the term of this patent is extended or adjusted under 35 U.S.C. 154(b) by 237 days.

(21) Appl. No.: 12/080,743

(22) Filed: Apr. 4, 2008

(65) Prior Publication Data

US 2010/0045277 A1    Feb. 25, 2010

Related U.S. Application Data

(62) Division of application No. 11/292,146, filed on Nov. 30, 2005, now abandoned, which is a division of application No. 10/441,976, filed on May 20, 2003, now abandoned.

(60) Provisional application No. 60/382,447, filed on May 21, 2002, provisional application No. 60/384,006, filed on May 28, 2002, provisional application No. 60/388,103, filed on Jun. 11, 2002.

(51) Int. Cl.
*G01N 27/72* (2006.01)
*G01N 27/82* (2006.01)
*G01N 33/12* (2006.01)

(52) U.S. Cl. ............ 324/209; 324/242; 324/243; 324/239

(58) Field of Classification Search ......... 324/209, 324/329, 242, 243
See application file for complete search history.

(56) References Cited

U.S. PATENT DOCUMENTS 6,657,429 B1 * 12/2003 Goldfine et al. ............ 324/232

OTHER PUBLICATIONS

Auld, B.A. and Moulder, J.C. (1999), "Review of Advances in Quantitative Eddy-Current Nondestructive Evaluation," Journal of Nondestructive Evaluation, vol. 18, No. 1.
Bozorth, R.M., Ferromagnetism, IEEE Press, 1978.
Bray, D.E., ed., Residual Stress Measurement and General Nondestructive Evaluation, PVP-vol. 429, ASME Pressure Vessels and Piping Conference, Atlanta, GA, ASME, 2001.
Grendahl, S. and R. Kilbane (2002), "Environmentally Assisted Cracking Concerns for Cadmium Replacement," presented at Tri-Service Corrosion Conference, 2002.

(Continued)

*Primary Examiner*—Reena Aurora
(74) *Attorney, Agent, or Firm*—Hamilton, Brook, Smith & Reynolds, P.C.

(57) ABSTRACT

Described are methods for monitoring of stresses and other material properties. These methods use measurements of effective electrical properties, such as magnetic permeability and electrical conductivity, to infer the state of the test material, such as the stress, temperature, or overload condition. The sensors, which can be single element sensors or sensor arrays, can be used to periodically inspect selected locations, mounted to the test material, or scanned over the test material to generate two-dimensional images of the material properties. Magnetic field or eddy current based inductive and giant magnetoresistive sensors may be used on magnetizable and/or conducting materials, while capacitive sensors can be used for dielectric materials. Methods are also described for the use of state-sensitive layers to determine the state of materials of interest. These methods allow the weight of articles, such as aircraft, to be determined.

18 Claims, 30 Drawing Sheets

OTHER PUBLICATIONS

Hydrogen in Metals, Proceedings of the Second Japan Institute of Metals, International Symposium, 1979.

Interrante, C. and Pressouyre, G. "Current Solutions to Hydrogen Problems in Steels," Proceedings of the First International Conference, ASM, 1982.

Lawrence, S.C. "Hydrogen Detection Gage," Hydrogen Embrittlement Testing, ASTM STP 543, 1974, pp. 83-105.

Doe Phase II Proposal, titled "Intelligent Probes for Enhanced Non-Destructive Determination of Degradation in Hot-Gas-Path Components," Topic #44c, dated Mar. 23, 2002.

Air Force Phase II Proposal, titled "Detection and Imaging of Damage, Including Hydrogen Embrittlement Effects in Landing Gear and Other High-Strength Steel Components," Topic #AF01-308, dated Apr. 9, 2002.

NASA Phase II Proposal, titled "Shaped Field Giant Magnetoresistive Sensor Arrays for Materials Testing," Topic #01-II A1.05-8767, dated May 2, 2002.

Navy Phase I Proposal, titled "Observability Enhancement and Uncertainty Mitigation for Engine Rotating Component PHM," Topic #N02-188, dated Aug. 14, 2002.

Final Report submitted to NASA, titled "Shaped Field Giant Magnetoresisitive Sensor Arrays for Materials Testing," dated May 3, 2002.

Final Report submitted to Air Force, titled "Detection and Imaging of Damage, Including Hydrogen Embrittlement Effects in Landing Gear and Other High-Strength Steel Components," dated Jul. 3, 2002.

Technical Report titled "MWM Examination of Twenty X2M Steel Fatigue Specimens After Abusive Grinding," US ARMY Final Report 08162002.

Technical paper titled "Friction Stir Weld Inspection through Conductivity Imaging using Shaped Field MWM®˜Arrays," Proceedings of the 6th International Conference on Trends in Welding, Callaway Gardens, GA; ASM International, Jan. 2003.

Technical paper titled "MWM Eddy Current Sensor Array Imaging of Surface and Hidden Corrosion for Improved Fleet Readiness and Cost Avoidance," presented at U.S. Army Corrosion Conference, Clearwater Beach; FL, Feb. 11-13, 2003.

Technical paper titled "Remote Temperature and Stress Monitoring Using Low Frequency Inductive Sensing," SPIE NDE/Health Monitoring of Aerospace Materials and Composites, San Diego, CA, Mar. 2-6, 2003.

Technical paper titled "In-Situ Crack Detection and Depth Discrimination for Coated Turbine Blade Contact Faces," presented at ASNT Spring Conference, Orlando, Florida, Mar. 10-14, 2003.

Technical paper titled "MWM Eddy Current Sensor Array Characterization of Aging Structures Including Hidden Damage Imaging," presented at the NACE Conference, San Diego; CA, Mar. 17-19, 2003.

Technical paper titled "Material Condition Monitoring Using Embedded and Scanning Sensors for Prognostics," presentation at the 57th MFPT Conference, Virginia Beach, VA; Apr. 2003.

Technical paper titled "Nondestructive Evaluation for Condition Based Maintenance and Prognostics & Health Monitoring of Legacy and New Platforms," 57th MFPT Conference, Virginia Beach, VA; Apr. 2003.

Technical paper titled "Validation of Multi-Frequency Eddy Current MWM Sensors and MWM-Arrays for Coating Production Quality and Refurbishment Assessment," submitted for the proceedings of the ASME/IGTI Turbo conference, Jun. 2003, Atlanta, GA.

Technical paper titled "Corrosion Detection and Prioritization Using Scanning and Permanently Mounted MWM Eddy-Current Arrays", Tri-Service Corrosion Conference, Jan. 2002.

Technical paper titled "Surface Mounted and Scanning Periodic Field Eddy-Current Sensors for Structural Health Monitoring," presented at IEEE Aerospace Conference: Prognostics & Health Management for Aging Aircraft; Mar. 2002.

Technical paper titled "MWM-Array Characterization and Imaging of Combustion Turbine Components," presented at EPRI International Conference on Advances in Life Assessment and Optimization of Fossil Power Plants, Orlando, FL; Mar. 2002.

Technical paper titled "Corrosion Detection and Prioritization Using Scanning and Permanently Mounted MWM Eddy-Current Arrays," presented at U.S. Army Corrosion Summit, Mar. 2002.

Technical paper titled "MWM-Array Characterization and Imaging of Combustion Turbine Components," presented at EPRI International Conference on Advances in Life Assessment and Optimization of Fossil Fuel Power Plants, Mar. 2002.

Technical paper titled "Applications of MWM Sensors and MWM-Arrays for Inspection of Aircraft Components," presented at NAVAIR NDT Working Group, Apr. 2002.

Technical paper titled "Application of MWM® Eddy Current Technology during Production of Coated Gas Turbine Components," presented at 11th International Symposium on Nondestructive Characterization of Materials, Berlin, Germany; Jun. 2002.

Technical paper titled "High Temperature Eddy-Current Sensors for Heat Treatment Monitoring," presented at AeroMat, Jun. 2002.

Technical paper titled "Eddy-Current Array Volumetric Imaging of Microstructure and Flaws for Thick Components," presented at AeroMat, Jun. 2002.

Technical paper titled "Absolute Electrical Property Imaging using High Resolution Inductive, Magnetoresistive and Capacitive Sensor Arrays for Materials Characterization," presented at 11th International Symposium on Nondestructive Characterization of Materials, Berlin, Germany; Jun. 2002.

Technical paper titled "Friction Stir Weld Inspection for Lack-of-Penetration Defects via Conductivity Mapping using MWM Eddy-Current Sensor Arrays," presented at AeroMat, Jun. 2002.

Technical paper titled "Eddy Current Sensor Technology for Real-Time State Monitoring, Condition Based Maintenance, and Life Management," presented at ONR Prognostics Workshop, Jul. 2002.

Technical paper titled "MWM-Array Eddy Current Sensors for Detection of Cracks in Regions with Fretting Damage," published in ASNT Materials Evaluation, vol. 60, No. 7, pp. 870-877; Jul. 2002.

Technical paper titled "Residual and Applied Stress Estimation from Directional Magnetic Permeability Measurements with MWM Sensors," published in ASME Journal of Pressure Vessel Technology, vol. 124, pp. 375-381; Aug. 2002.

Technical paper titled "Rapid High-Resolution Corrosion Imaging and Detection with MWM Eddy Current Arrays," presented at 5th International Aircraft Corrosion Conference, Aug. 2002.

Technical paper titled "High-Resolution, Deep Penetration and Rapid GMR/Eddy Current Array Imaging of Weld Condition and Quality" presented at ASNT Structural Materials Technology—NDE/NDT for Highways and Bridges, Sep. 2002.

Technical paper titled "High Resolution MWM-Array Imaging of Cracks in Fretting Regions of Engine Disk Slots," presented at the 6th Joint FAA/DoD/NASA Aging Aircraft Conference, Sep. 2002.

Technical paper titled "Multi-Site Damage Imaging of 3rd Layer Cracks in Lap Joints using MWM-Arrays," presented at the 6th Joint FAA/DoD/NASA Aging Aircraft Conference, Sep. 2002.

Technical paper titled "Conformable Eddy-Current Sensors and Arrays for Fleetwide Gas Turbine Component Quality Assessment," published in ASME Journal of Engineering for Gas Turbines and Power, vol. 124, No. 4, pp. 904-909; Oct. 2002.

Technical paper titled "MWM-Array Eddy Current Testing for Corrosion and Fatigue Damage," presented at Air Transport Association, Oct. 2002.

Technical paper titled "Characterization and Imaging of Coated Turbine Components with MWM Sensors and MWM-Arrays," presented at ASM Heat Treat/Surface Engineering, Oct. 2002.

Technical paper titled "Thin, Conformable Eddy Current Sensor Arrays for Difficult-to-Access Location Inspections," presented at Defense Working Group, Nov. 2002.

Technical paper titled "Health Monitoring for Landing Gear and Other Critical Components," presented at ASIP 2002, Dec. 2002.

Technical paper titled "MWM-Eddy-Current Arrays for Crack Initiation and Growth Monitoring," submitted to International Journal of Fatigue, from the International Conference on Fatigue Damage of Structural Materials IV, Hyannis, MA, 2002.

* cited by examiner

US 7,876,094 B2

MAGNETIC FIELD CHARACTERIZATION OF STRESSES AND PROPERTIES IN MATERIALS

RELATED APPLICATIONS

This application is a divisional of U.S. application Ser. No. 11/292,146, filed Nov. 30, 2005, now abandoned which is a divisional of U.S. application Ser. No. 10/441,976, filed May 20, 2003, now abandoned which claims the benefit of U.S. Provisional Application No. 60/382,447, filed May 21, 2002, U.S. Provisional Application No. 60/384,006, filed May 28, 2002, and U.S. Provisional Application No. 60/388,103, filed Jun. 11, 2002.

The entire teachings of the above applications are incorporated herein by reference.

GOVERNMENT SUPPORT

The invention was supported, in whole or in part, by a grant F09650-01-M-0956 from the U.S. Air Force. The Government has certain rights in the invention.

BACKGROUND OF THE INVENTION

The technical field of this application is that of nondestructive materials characterization, particularly quantitative, model-based characterization of surface, near-surface, and bulk material condition for flat and curved parts or components using magnetic field based or eddy-current sensors. Characterization of bulk material condition includes (1) measurement of changes in material state, i.e., degradation/damage caused by fatigue damage, creep damage, thermal exposure, or plastic deformation; (2) assessment of residual stresses and applied loads; and (3) assessment of processing-related conditions, for example from aggressive grinding, shot peening, roll burnishing, thermal-spray coating, welding or heat treatment. It also includes measurements characterizing material, such as alloy type, and material states, such as porosity and temperature. Characterization of surface and near-surface conditions includes measurements of surface roughness, displacement or changes in relative position, coating thickness, temperature and coating condition. Each of these includes detection of electromagnetic property changes associated with either microstructural and/or compositional changes, or electronic structure (e.g., Fermi surface) or magnetic structure (e.g., domain orientation) changes, or with single or multiple cracks, cracks or stress variations in magnitude, orientation or distribution.

A specific application of these techniques is the inspection of high-strength steel components with the goal of measuring applied and residual stresses and detecting early stage fatigue damage or hydrogen embrittlement. Highly stressed aircraft components, such as landing gear components, require the use of steels such as 4340M and 300M heat treated to very high strength levels. The integrity of these components is critical to the safe operation of aircraft and for maintaining readiness of military aircraft. However, unintentional loading of these components, such as a hard landing, can impart residual stresses that compromise the integrity of the component. Similarly, the mechanical properties of these ultra-high strength steels can be seriously degraded as a result of the ingress of hydrogen. Hydrogen ingress can occur during pickling or plating operations and also during cleaning with citric acid based maintenance solutions. The resulting hydrogen embrittlement is unpredictable and can cause catastrophic failure of the component. Hydrogen embrittlement has been established as the direct cause of numerous landing gear failures. This similarly applies to related degradation mechanisms such as temper embrittlement, creep and other degradation processes that reduce a materials functional behavior.

The detrimental effects of hydrogen on material properties and component integrity have been observed in a wide range of metals, as described for example in Interrante and in Hydrogen in Metals. Management of high-strength steel components embrittled by hydrogen is made more difficult by the fact that failures are typically delayed, occurring some time after ingress of atomic hydrogen. The delay between exposure to hydrogen and failure of a high strength steel component depends on a number of factors. Among these are the levels of hydrogen concentration, tensile stress, temperature, stress gradients, and certain impurities in the steel, as well as the type, concentration, and size of certain crystal lattice defects and inclusions. Moreover, susceptibility to hydrogen embrittlement can vary significantly between different heats of steels and between different pours from a given heat, as described by Lawrence. Hydrogen concentration on the order of a few parts per million is sufficient to cause hydrogen embrittlement and delayed fracture. Once atomic hydrogen enters the steel, excess hydrogen atoms diffuse to inclusions, preexisting defects, and zones of high dislocation density. Some hydrogen atoms, as a result of stress-assisted diffusion, can cluster and form "platelets" leading to initiation of microcracks. When such platelets form in front of a crack tip, they facilitate crack extension. Critical regions where hydrogen cracks are more likely to initiate are notches or other stress raisers where local hydrogen concentration is higher due to enhanced diffusion into the triaxially stressed region in front of a stress raiser. Cracks at these critical locations often initiate close to but beneath the surface, making them more difficult to detect.

A recent review of existing magnetic/electromagnetic, diffraction, ultrasonic and other methods for assessment of residual stresses in steel components by Bray highlighted strengths and weaknesses of the available methods. This review also indicated that practical and cost-effective methods for assessment of residual stresses as well as for monitoring of applied stresses over wide areas in steel components are not yet available. Typically, discrete strain gages are mounted directly onto the material under test (MUT). However this requires intimate fixed contact between the strain gage and the MUT and individual connections to each of the strain gages, both of which limit the potential usefulness for monitoring stress over large areas. Furthermore, strain gages are limited in durability and do not always provide sufficient warning of gage failure or malfunction. Possible correlations between magnetic properties and stresses in ferromagnetic materials have been studied for over 100 years, as reviewed by Bozorth. Magnetostriction effect data suggests that, depending on the magnitude and sign of the magnetostriction coefficient, correlation between stress and magnetic permeability within certain ranges of the magnetic field should be present. However, attempts to use conventional inductive, i.e., eddy-current sensors for assessment of residual stresses as well as for a number of other applications have shown serious limitations, particularly for complex geometry components.

Conventional eddy-current sensing involves the excitation of a conducting winding, the primary, with an electric current source of prescribed frequency. This produces a time-varying magnetic field at the same frequency, which in turn is detected with a sensing winding, the secondary. The spatial distribution of the magnetic field and the field measured by the secondary is influenced by the proximity and physical properties (electrical conductivity and magnetic permeability) of nearby materials. When the sensor is intentionally placed in close proximity to a test material, the physical properties of the material can be deduced from measurements of the impedance between the primary and secondary windings. Traditionally, scanning of eddy-current sensors across the material surface is then used to detect flaws, such as cracks. Conventional eddy-current sensors widely used in nondestructive testing applications are effective at examining near surface properties of materials, but have a limited capability to examine material property variations deep within a material. In contrast, ultrasonic techniques that are also widely used are effective at measuring property variations deep within a material, but have limited sensitivity near the surface and behind some geometric features such as air gaps.

SUMMARY OF THE INVENTION

Aspects of the embodiment of the invention described herein involve novel sensors and sensor arrays for the measurement of the near surface properties of conducting and/or magnetic materials. These sensors and arrays use novel geometries for the primary winding and sensing elements that promote accurate modeling of the response and provide enhanced observability of property changes of the test material.

Methods are described herein for the monitoring of material properties as they are changed during processing. This can involve disposing an eddy current sensor or sensor array in proximity to the test material and converting the response of each sensor or sense element into an effective material property. In one embodiment, the sense elements are sensing coils the respond to absolute changes in the magnetic field response. Preferably, these coils are rectangular. In another embodiment, the sense elements incorporate GMR sensors. In a preferred embodiment, the leads to the sense elements also have a proximate set of leads that permit cancellation of the stray magnetic flux to the leads and permits the use of small sense elements. In one embodiment of the invention, the process being monitored is the heat treatment of a material. In one embodiment, the effective property is the electrical conductivity. In another, it is the lift-off. In one embodiment, the measurements are performed at multiple excitation frequencies. In another embodiment, the sensor is not in contact with the surface of the test material, which helps to minimize any effects the monitoring system may have on the environment around the material being processed.

Another aspect of the invention includes methods for monitoring stresses in materials. Preferably, this is performed with eddy current sensors disposed in proximity to the surface of the test material or embedded within layers of the test material. In one embodiment, measurements are performed with multiple orientations of the sensor relative the stress distribution. In another embodiment, the measurement orientations are perpendicular. Preferably, the orientations correspond to the maximum and minimum principal stresses, or to maximum and minimum property values that are to be determined. In yet another embodiment, the sensor or sensor array is mounted on a flexible substrate. The sensor can have a foam backing, which permits sensor conformability to the test material surface, or a rigid backing that approximates the shape of the material surface and permits contact or non-contact measurements. In one embodiment, the sensor has a plurality of sense elements which may be aligned with one another. In another embodiment, the sensor is scanned over the surface, preferably in multiple orientations, so that the entire stress distribution and orientation of stresses over the material can be resolved. In a preferred embodiment, the sensor arrays are scanned in two mutually perpendicular orientations, preferably with the orientations corresponding to the directions of maximum and minimum principal stresses.

Alternatively, the sensors or sensor arrays can be mounted in one or more locations to monitor the stresses. When at least two sensors are mounted in different locations, the sensors can have different orientations. Preferably, the orientations are mutually perpendicular, which also permits the monitoring of maximum and minimum principal stresses. In one embodiment, stress measurements are performed at multiple excitation frequencies. In another embodiment, the electrical property of interest is the magnetic permeability.

Other aspects of the invention include methods for the inspection of magnetic materials. In one embodiment, an eddy current sensor is placed proximate to a test material to measure the magnetic permeability. In one embodiment, the sensor response is measured at multiple locations to determine the magnetic permeability distribution of the material surface. In another embodiment, the permeability is measured with different sensor orientations, in another it is measured with sensors placed at different locations. In one embodiment, the sensor has a plurality of sense elements that may be aligned with one another. In another embodiment, the sensor is scanned over the surface, preferably in multiple orientations, so that the material property distribution and orientation over the material can be resolved. In another embodiment, the sensor array is mounted to the surface. Preferably, at least one more sensor array is mounted with a different orientation.

Yet another method is described for the monitoring of the weight of an article, by measuring the magnetic permeability of a portion of the test material that transfers the mechanical load from the article and correlating this permeability with the article weight. Preferably, the article is an aircraft. In one embodiment, measurements are performed at several select locations on the material. In one embodiment, the sensors are mounted to the material In another, the sensors are scanned over the surface of the material. Preferably, the sensors are scanned so that the permeability is measured in a direction that is parallel to the direction of maximum principal stress.

Also described are methods for monitoring of the state of a material or a test article. In one embodiment, a sensor is placed in proximity to a test material to measure an electrical property of the state of the article. In one embodiment, the electrical property is the magnetic permeability and in another the electrical property is the electrical conductivity. In one embodiment, the state is stress and in another it is temperature. In another embodiment the state is an overload condition. Preferably, this overload condition results from excessive temperature expose as a thermal overload or from over stressing as a mechanical overload. Alternatively, the state can reflect the accumulation of fatigue damage of the presence of a crack within the test article. In another embodiment, the state of the article may be inferred from state-sensitive material layers. These layers may be placed on the surface of the article or embedded within layers of the article. In one embodiment, the state-sensitive material can be split into strips or some other geometry that facilitates a rapid inspection or indication of state changes. Preferably, the strips have different orientations with depth into the test article so that the depth of the state change can also be readily determined. In a further embodiment, these methods are used to remotely monitor the state or properties of a hidden material so that other material layers are present between the sensor and the material layer of interest.

In one embodiment for monitoring the properties of the materials, the sensors can be eddy current sensors. In one embodiment, the sensors have separate layers for the drive winding and sense elements. In another embodiment, the conductors for the drive and sense elements are placed in different layers on the test article itself. In another embodiment, the sensor is an array of eddy current sensors. These sensors can be mounted to the surface of the material or scanned over the surface of the article. In another embodiment, the sensor is a dielectric sensor. In another, it is a GMR sensor. These sensors can also be protected from environmental damage by durable layers. Suitable durable materials depend upon the type of sensor and the environment. In one embodiment, the durable medium is a ceramic. In another, it is a stainless steel.

BRIEF DESCRIPTION OF THE DRAWINGS

The foregoing and other objects, features and advantages of the embodiment of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the embodiment of the invention.

DETAILED DESCRIPTION OF THE INVENTION

Figure 1:
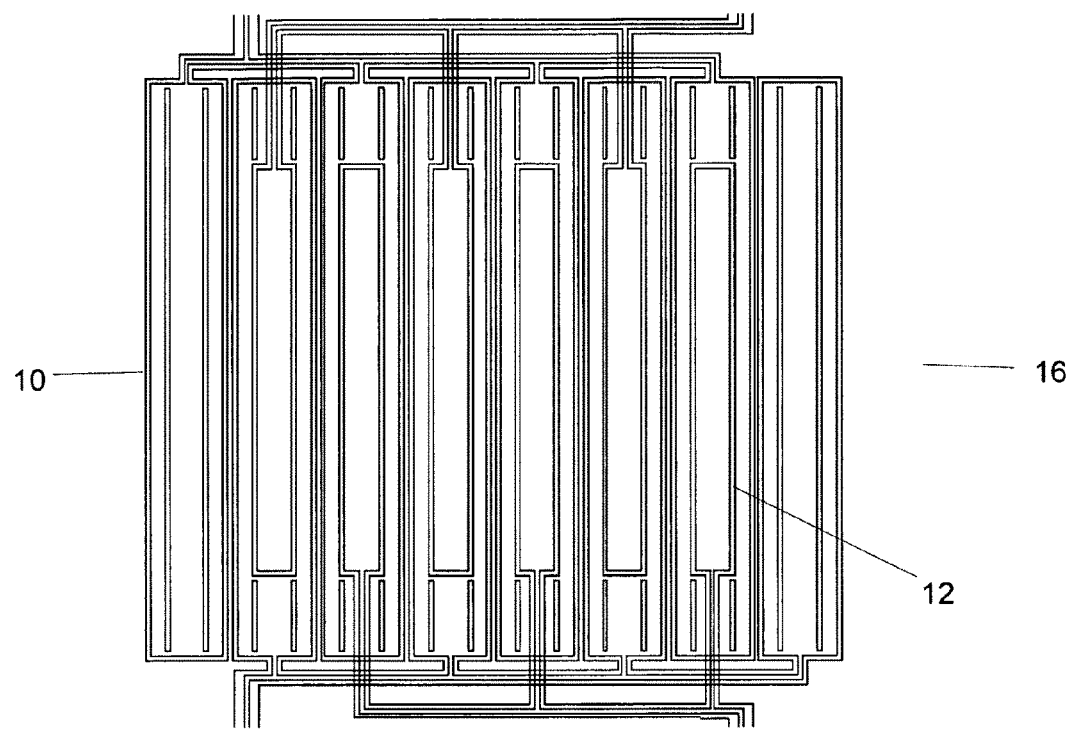
FIG. 1 is a drawing of a spatially periodic field eddy-current sensor.

A description of preferred embodiments of the invention follows.

The use of conformable and nonconformable eddy-current sensors and sensor arrays is described herein for the nondestructive characterization of materials, particularly as it applies to the characterization of applied and residual stresses. This includes surface mounted and scanning, contact and non contact configuration. This sensing approach can be used to monitor the material characteristics at a given location with single or multiple sensing element sensors, sensor arrays and/or networks of surface mounted sensors using hand-held probes, mounted into automated scanners or as part of an embedded network. The sensors can be mounted into a structure in proximity to a material under test for monitoring the property changes while the material is being stressed and fatigued. Alternatively, such embedded sensors can be queried with instrumentation on a scheduled or unscheduled basis with either no electronics on board or minimal electronics on board, and by plugging in at an easy access location. The sensors can also be used to detect process related changes in the material properties, such as grinding burns in steels either as a part of in-process monitoring or at any time after processing, i.e., during quality control inspections or in service.

Aspects of this embodiment of the invention address measurement of damage, conditions (e.g., from manufacture, rework or repair), stresses microstructure changes and other material properties through scanning in contact on non-contact surface mounting, non contact mounting and even monitoring one layer or on internal material property through another layer or external material closer to the sensor. Applications include but are not limited to test materials, coupons, components or systems, bridges, aircraft (e.g., landing gear), towers, construction equipment, nuclear reactor nozzles (e.g., I.D. or O.D., or J-welds), submarines (e.g., temper embrittlement near welds) automobile components, tires (e.g., internal steel components), medical devices or implants, and weapon casings.

A conformable eddy-current sensor suitable for these measurements, the Meandering Winding Magnetometer (MWM®), is described in U.S. Pat. Nos. 5,015,951, 5,453,689, and 5,793,206. The MWM is a "planar," conformable eddy-current sensor that was designed to support quantitative and autonomous data interpretation methods. These methods, called grid measurement methods, permit crack detection on curved surfaces without the use of crack standards, and provide quantitative images of absolute electrical properties (conductivity and permeability) and coating thickness without requiring field reference standards (i.e., calibration is performed in "air," away from conducting surfaces). MWM sensors and MWM-Arrays can be used for a number of applications, including fatigue monitoring and inspection of structural components for detection of flaws, degradation and microstructural variations as well as for characterization of coatings and process-induced surface layers. Characteristics of these sensors and sensor arrays include directional multi-frequency magnetic permeability or electrical conductivity measurements over a wide range of frequencies, e.g., from 250 Hz to 40 MHz with the same MWM sensor or MWM-Array, high-resolution imaging of measured permeability or conductivity, rapid permeability or conductivity measurements with or without a contact with the surface, and a measurement capability on complex surfaces with a hand-held probe or with an automated scanner. This allows the assessment of applied and residual stresses as well as permeability variations in a component introduced from processes such as grinding operations.

FIG. 1 illustrates the basic geometry of an the MWM sensor 16, a detailed description of which is given in U.S. Pat. Nos. 5,453,689, 5,793,206, and 6,188,218 and U.S. patent application Ser. Nos. 09/666,879 and 09/666,524, both filed on Sep. 20, 2000, the entire teachings of which are incorporated herein by reference. The sensor includes a primary winding 10 having extended portions for creating the magnetic field and secondary windings 12 within the primary winding for sensing the response. The primary winding is fabricated in a spatially periodic pattern with the dimension of the spatial periodicity termed the spatial wavelength λ. A current is applied to the primary winding to create a magnetic field and the response of the MUT to the magnetic field is determined through the voltage measured at the terminals of the secondary windings. This geometry creates a magnetic field distribution similar to that of a single meandering winding. A single element sensor has all of the sensing elements connected together. The magnetic vector potential produced by the current in the primary can be accurately modeled as a Fourier series summation of spatial sinusoids, with the dominant mode having the spatial wavelength λ. For an MWM-Array, the responses from individual or combinations of the secondary windings can be used to provide a plurality of sense signals for a single primary winding construct as described in U.S. Pat. No. 5,793,206 and Re. 36,986.

Figure 2:
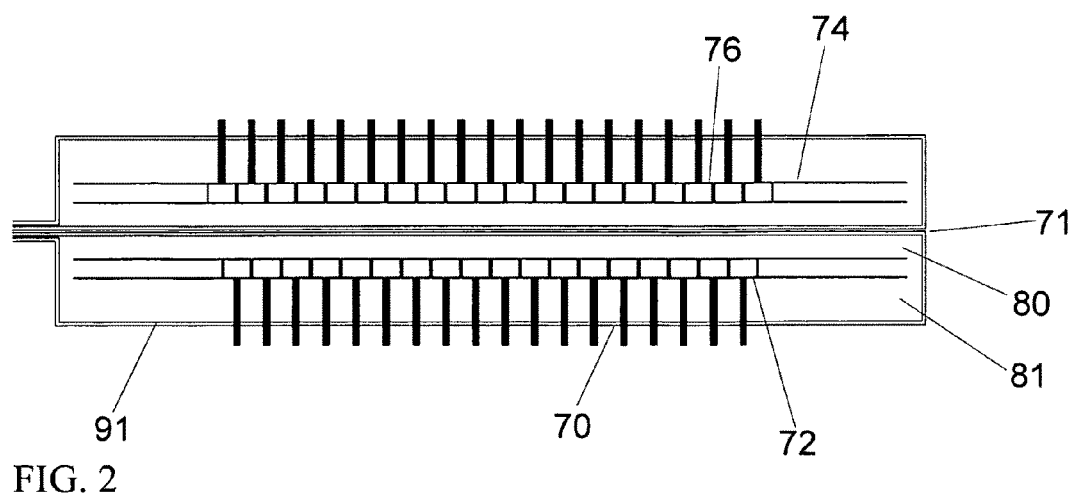
FIG. 2 is an expanded view of the drive and sense elements for an eddy-current array having offset rows of sensing elements.
Figure 3:
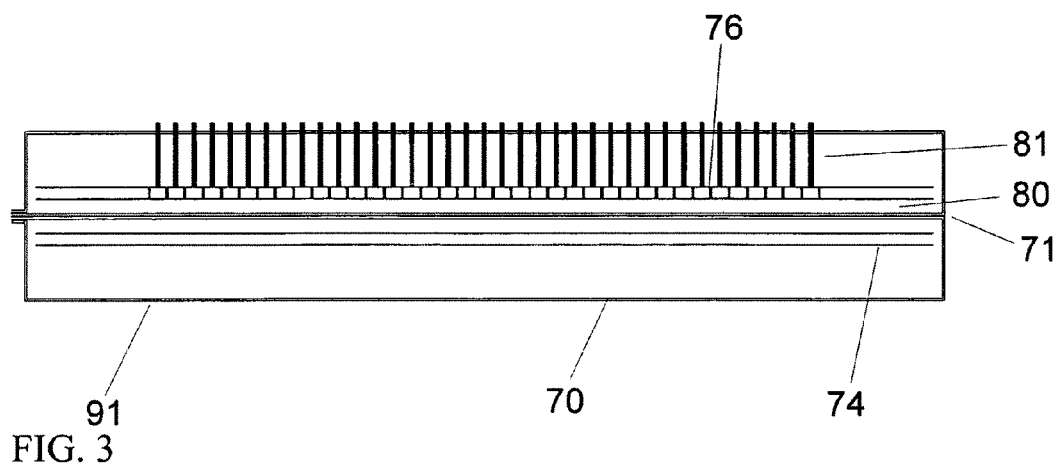
FIG. 3 is an expanded view of the drive and sense elements for an eddy-current array having a single row of sensing elements.
Figure 4:
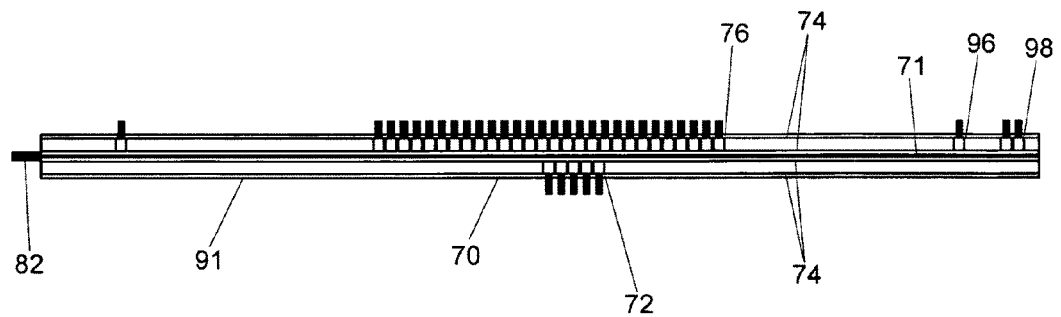
FIG. 4 is an expanded view of an eddy-current array where the locations of the sensing elements along the array are staggered.

In another embodiment, eddy-current sensor arrays comprised of one or more drive windings, (possibly a single rectangle) and multiple sensing elements are used to inspect the test material. Example sensor arrays are shown in FIG. 2 through FIG. 4 some embodiments of which are described in detail in U.S. patent application Ser. No. 10/102,620, filed Mar. 19, 2002, and Ser. No. 10/010,062, filed Mar. 13, 2001, the entire teachings of which are incorporated herein by reference. These arrays include a primary winding 70 having extended portions for creating the magnetic field and a plurality of secondary elements 76 within the primary winding for sensing the response to the MUT. The secondary elements are pulled back from the connecting portions of the primary winding to minimize end effect coupling of the magnetic field. Dummy elements 74 can be placed between the meanders of the primary to maintain the symmetry of the magnetic field, as described in U.S. Pat. No. 6,188,218. When the sensor is scanned across a part or when a crack propagates across the sensor, perpendicular to the extended portions of the primary winding, secondary elements 72 in a primary winding loop adjacent to the first array of sense elements 76 provide a complementary measurement of the part properties. These arrays of secondary elements 72 can be aligned with the first array of elements 76 so that images of the material properties will be duplicated by the second array (improving signal-to-noise through combining the responses or providing sensitivity on opposite sides of a feature such as a fastener as described in—U.S. patent application Ser. Nos. 10/102,620 and 10/010,062. Alternatively, to provide complete coverage when the sensor is scanned across a part the sensing elements, can be offset along the length of the primary loop or when a crack propagates across the sensor, perpendicular to the extended portions of the primary winding, as illustrated in FIG. 2.

The dimensions for the sensor array geometry and the placement of the sensing elements can be adjusted to improve sensitivity for a specific inspection. For example, the effective spatial wavelength or four times the distance 80 between the central conductors 71 and the sensing elements 72 can be altered to adjust the sensitivity of a measurement for a particular inspection. For the sensor array of FIG. 2, the distance 80 between the secondary elements 72 and the central conductors 71 is smaller than the distance 81 between the sensing elements 72 and the return conductor 91. An optimum response can be determined with models, empirically, or with some combination of the two. An example of a modified sensor design is shown FIG. 3. In this sensor array, all of the sensing elements 76 are on one side of the central drive windings 71. The size of the sensing elements and the gap distance 80 to the central drive windings 71 are the same as in the sensor array of FIG. 2. However, the distance 81 to the return of the drive winding has been increased, as has the drive winding width to accommodate the additional elements in the single row of elements. Increasing the distance to the return reduces the size of the response when the return crosses a feature of interest such as a crack. Another example of a modified design is shown in FIG. 4. Here, most of the sensing elements 76 are located in a single row to provide the basic image of the material properties. A small number of sensing elements 72 are offset from this row to create a higher image resolution in a specific location. Other sensing elements are distant from the main grouping of sensing elements at the center of the drive windings to measure relatively distant material properties, such as the base material properties for plates at a lap joint or a weld.

Figure 5:
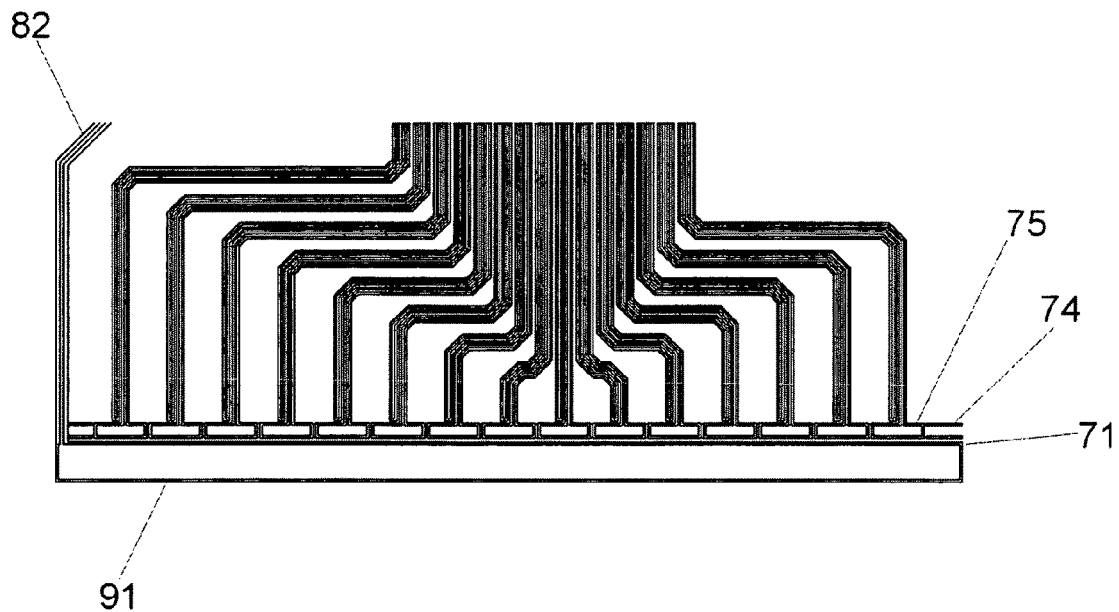
FIG. 5 is an expanded view of an eddy current array with a single rectangular loop drive winding and a linear row of sense elements on the outside of the extended portion of the loop.

In one embodiment, the number of conductors used in the primary winding can be reduced further so that a single rectangular drive is used. As shown in FIG. 5, a single loop having extended portions is used for the primary winding. A row of sensing elements 75 is placed on the outside of one of the extended portions. This is similar to designs described in U.S. Pat. No. 5,453,689 where the effective wavelength of the dominant spatial field mode is related to the spacing between the drive winding and sensing elements. This spacing can be varied to change the depth of sensitivity to properties and defects. In one embodiment this distance is optimized using models to maximize sensitivity to a feature of interest such as a buried crack or stress at a specific depth. Advantages of the design in FIG. 5 include a narrow drive and sense structure that allows measurements close to material edges and non-crossing conductor pathways so that a single layer design can be used with all of the conductors in the sensing region in the same plane. The width of the conductor 91 farthest from the sensing elements can be made wider in order to reduce an ohmic heating from large currents being driven through the drive winding. In another embodiment additional rows of sense elements can be placed on the opposite side of the drive 71 at the same or different distances from the drive. In another embodiment sensing elements can be placed in different layers to provide multiple lift-offs at the same or different positions.

The MWM sensor and sensor array structure can be produced using micro-fabrication techniques typically employed in integrated circuit and flexible circuit manufacture. This results in highly reliable and highly repeatable (i.e., essentially identical) sensors, which has inherent advantages over the coils used in conventional eddy-current sensors. As indicated by Auld and Moulder, for conventional eddy-current sensors "nominally identical probes have been found to give signals that differ by as much as 35%, even though the probe inductances were identical to better than 2%" [Auld, 1999]. This lack of reproducibility with conventional coils introduces severe requirements for calibration of the sensors (e.g., matched sensor/calibration block sets). In contrast, duplicate MWM sensor tips have nearly identical magnetic field distributions around the windings as standard micro-fabrication (etching) techniques have both high spatial reproducibility and resolution. As the sensor was also designed to produce a spatially periodic magnetic field in the MUT, the sensor response can be accurately modeled which dramatically reduces calibration requirements. For example, calibration in air can be used to measure an absolute electrical conductivity without calibration standards, which makes the sensor geometry well-suited to surface mounted or embedded applications where calibration requirements will be necessarily relaxed.

For applications at temperatures up to 120° C. (250° F.), the windings are typically mounted on a thin and flexible substrate, producing a conformable sensor. A higher temperature version has shown a good performance up to about 270° C. (520° F.). In another embodiment these sensors might be fabricated on ceramic substrates or with platinum leads and Boron Nitrite coatings or other means to extend their operating temperature range. The sensors, which are produced by microfabrication techniques, are essentially identical resulting in highly reliable and highly repeatable performance with inherent advantages over the coils used in conventional eddy-current sensors providing both high spatial reproducibility and resolution. For conformable sensors, the insulating layers can be a flexible material such as Kapton™, a polyimide available from E. I. DuPont de Nemours Company, while for high temperature applications the insulating layers can be a ceramic such as alumina.

For measuring the response of the individual sensing elements in an array, multiplexing between the elements can be performed. However, this can significantly reduce the data acquisition rate so a more preferably approach is to use an impedance measurement architecture that effectively allows the acquisition of data from all of the sense elements in parallel. Furthermore, ability to measure the MUT properties at multiple frequencies extends the capability of the inspection to better characterize the material and/or geometric properties under investigation. This type of instrument is described in detail in U.S. patent application Ser. No. 10/155,887, filed May 23, 2002, the entire teachings of which are incorporated herein by reference. The use of multiple sensing elements with one meandering drive and parallel architecture measurement instrumentation then permits high image resolution in real-time and sensitivity with relatively deep penetration of fields into MUT.

An efficient method for converting the response of the MWM sensor into material or geometric properties is to use grid measurement methods. These methods map the magnitude and phase of the sensor impedance into the properties to be determined and provide for a real-time measurement capability. The measurement grids are two-dimensional databases that can be visualized as "grids" that relate two measured parameters to two unknowns, such as the magnetic permeability (or electrical conductivity) and lift-off (where lift-off is defined as the proximity of the MUT to the plane of the MWM windings). For the characterization of coatings or surface layer properties, three- (or more)-dimensional versions of the measurement grids called lattices and hypercubes, respectively, can be used. Alternatively, the surface layer parameters can be determined from numerical algorithms that minimize the least-squares error between the measurements and the predicted responses from the sensor, or by intelligent interpolation search methods within the grids, lattices or hypercubes.

An advantage of the measurement grid method is that it allows for real-time measurements of the absolute electrical properties of the material and geometric parameters of interest. The database of the sensor responses can be generated prior to the data acquisition on the part itself, so that only table lookup and interpolation operations, which are relatively fast, needs to be performed. Furthermore, grids can be generated for the individual elements in an array so that each individual element can be lift-off compensated to provide absolute property measurements, such as the electrical conductivity. This again reduces the need for extensive calibration standards. In contrast, conventional eddy-current methods that use empirical correlation tables that relate the amplitude and phase of a lift-off compensated signal to parameters or properties of interest, such as crack size or hardness, require extensive calibrations using standards and instrument preparation.

Figure 6:
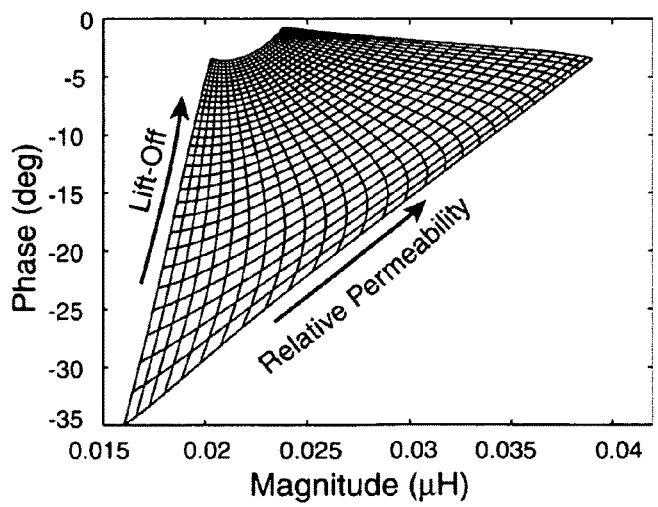
FIG. 6 shows a representative measurement grid relating the magnitude and phase of the sensor terminal impedance to the lift-off and magnetic permeability.
Figure 7:
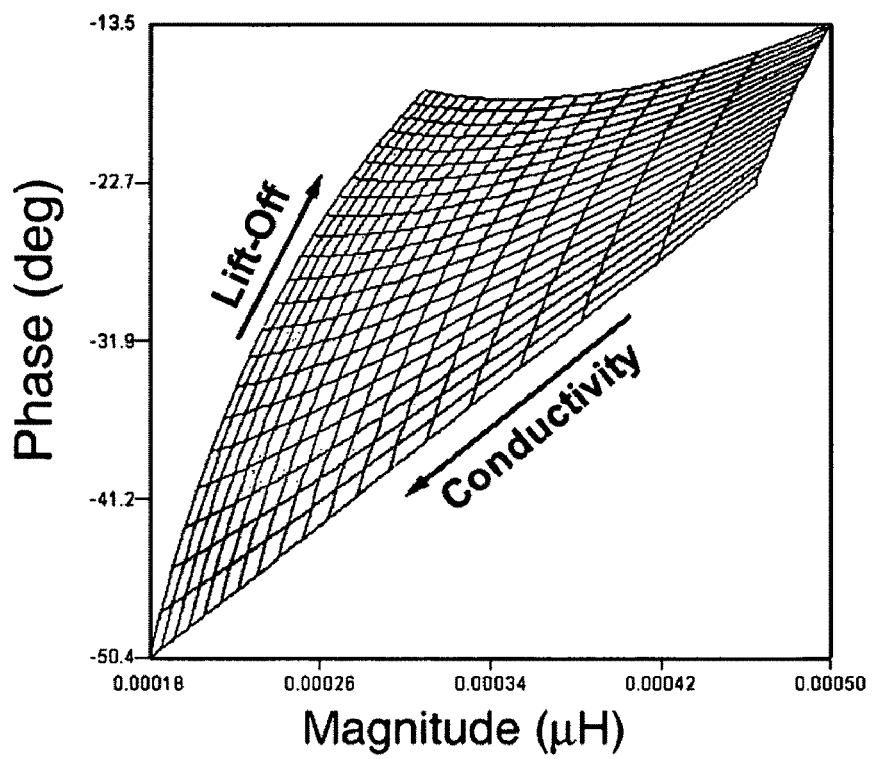
FIG. 7 shows a representative measurement grid relating the magnitude and phase of the sensor terminal impedance to the lift-off and electrical conductivity.

For ferromagnetic materials, such as most steels, a measurement grid provides conversion of raw data to magnetic permeability and lift-off. A representative measurement grid for ferromagnetic materials (e.g., carbon and alloy steels) is illustrated in FIG. 6. A representative measurement grid for a low-conductivity nonmagnetic alloy (e.g., titanium alloys, some superalloys, and austenitic stainless steels) is illustrated in FIG. 7. For coated materials, such as cadmium and cadmium alloys on steels, the properties of the coatings can be incorporated into the model response for the sensor so that the measurement grid accurately reflects, for example, the permeability variations of substrate material with stress and the lift-off. Lattices and hypercubes can be used to include variations in coating properties (thickness, conductivity, permeability), over the imaging region of interest. In one embodiment, the variation in the coating is corrected at each point in the image to improve the measurement of permeability in the substrate for the purpose of imaging stresses.

Robust directional magnetic permeability measurements by MWM sensors and MWM-Arrays with grid methods allow estimation of stresses by taking advantage of the magnetostriction effect. For steels, at magnetic fields typical of those used for MWM, the magnetostriction coefficient generally is positive, so that the magnetic permeability increases with stress. Thus, once a correlation between stress and MWM measured magnetic permeability is established, stresses can be estimated as long as baseline information is available. In another embodiment, bias fields or DC offsets in the drive current (possibly using a multiple turn wound or etched drive winding) can be used to move up the B-H curve away from the zero field location to improve performance.

Figure 8:
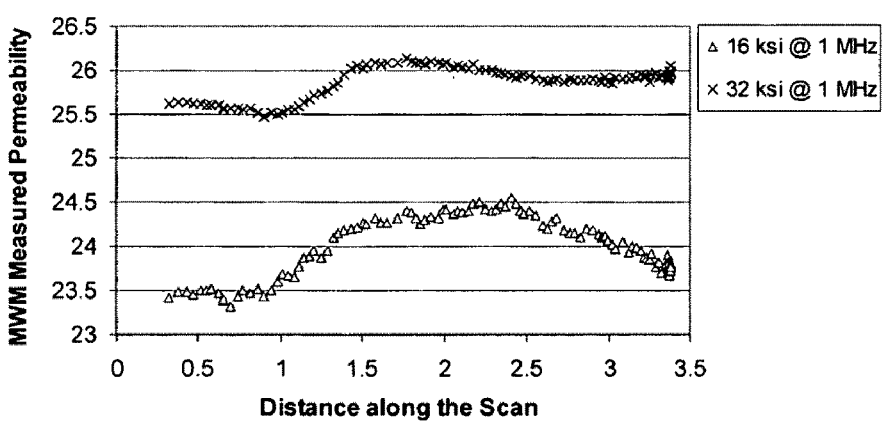
FIG. 8 shows a plot of MWM measured permeability scans along the axis of a 4340 steel tensile specimen containing semicircular notches, at two levels of applied stress. The distance along the scan is in inches.
Figure 9:
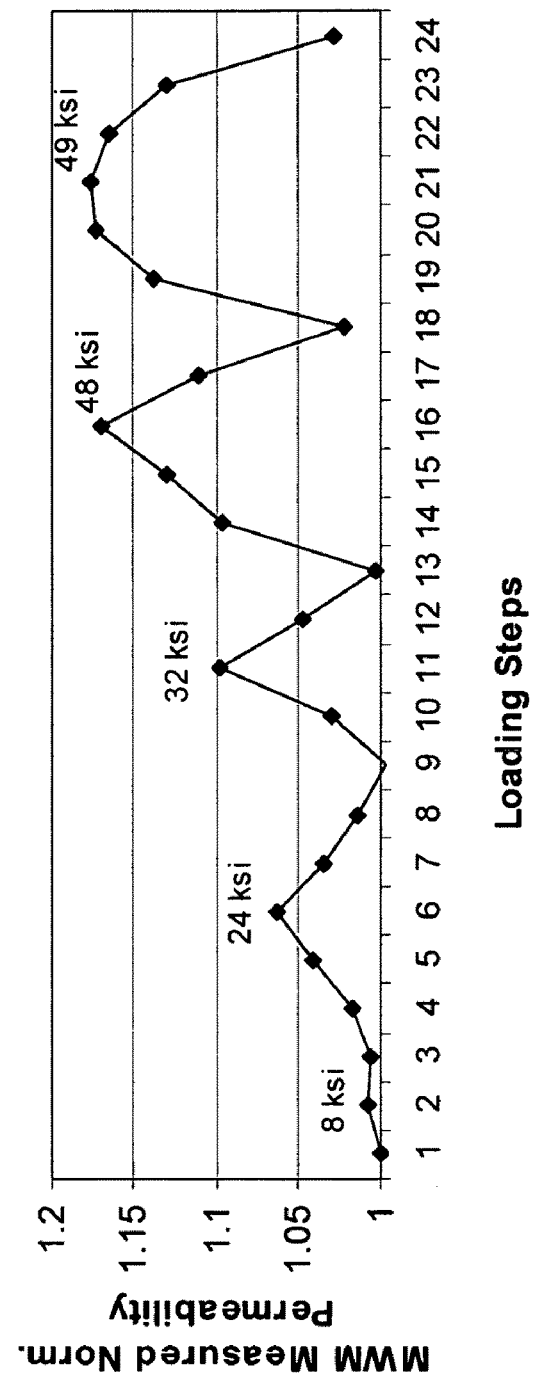
FIG. 9 shows a plot of MWM measured permeability for a five load-unload sequence.
Figure 10:
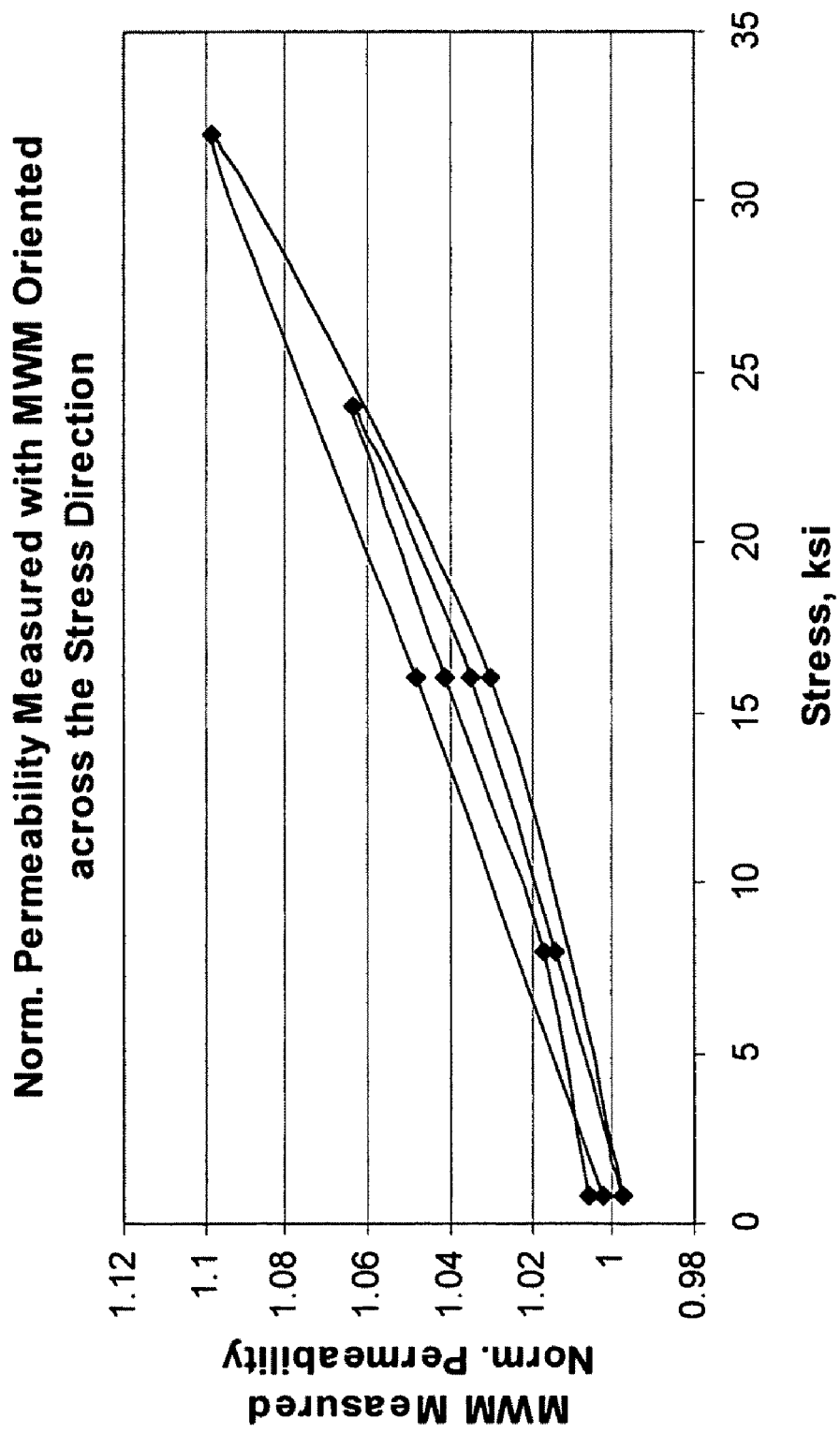
FIG. 10 shows a plot of MWM measured permeability for the loads achieved on the increasing and decreasing portions of a load-unload sequence.

An example of a permeability measurement scan with a single element sensor over a 4340 steel dogbone specimen with semicircular notches installed in a 90 kN (20,000-lb) Instron frame is shown in FIG. 8. In this case, the highest stress is expected at the 1.75-in. position with the highest estimated nominal stress in the narrow section between the semicircular notches at 16 and 32 ksi, respectively. Magnetic permeability measurements were performed prior to each loading sequence, i.e., at no load and at various levels of tensile load in an incremental load-unload sequence. The results shown in FIG. 8 were obtained at a frequency of 1 MHz. Multiple frequency MWM measurements can provide information on stress distribution with depth. FIG. 9 shows permeability changes in five load-unload sequences to a maximum estimated nominal stress of 8, 24, 32, 48, and 49 ksi. The pattern of the magnetic permeability changes actually reflects the loading pattern. The permeability-load curves shown in FIG. 10 illustrates a hysteresis between permeability measured at loads achieved on the increasing and decreasing portions of a loading sequence. This hysteresis is caused by a "delay" in rotation of magnetic domains on unloading.

Figure 11:
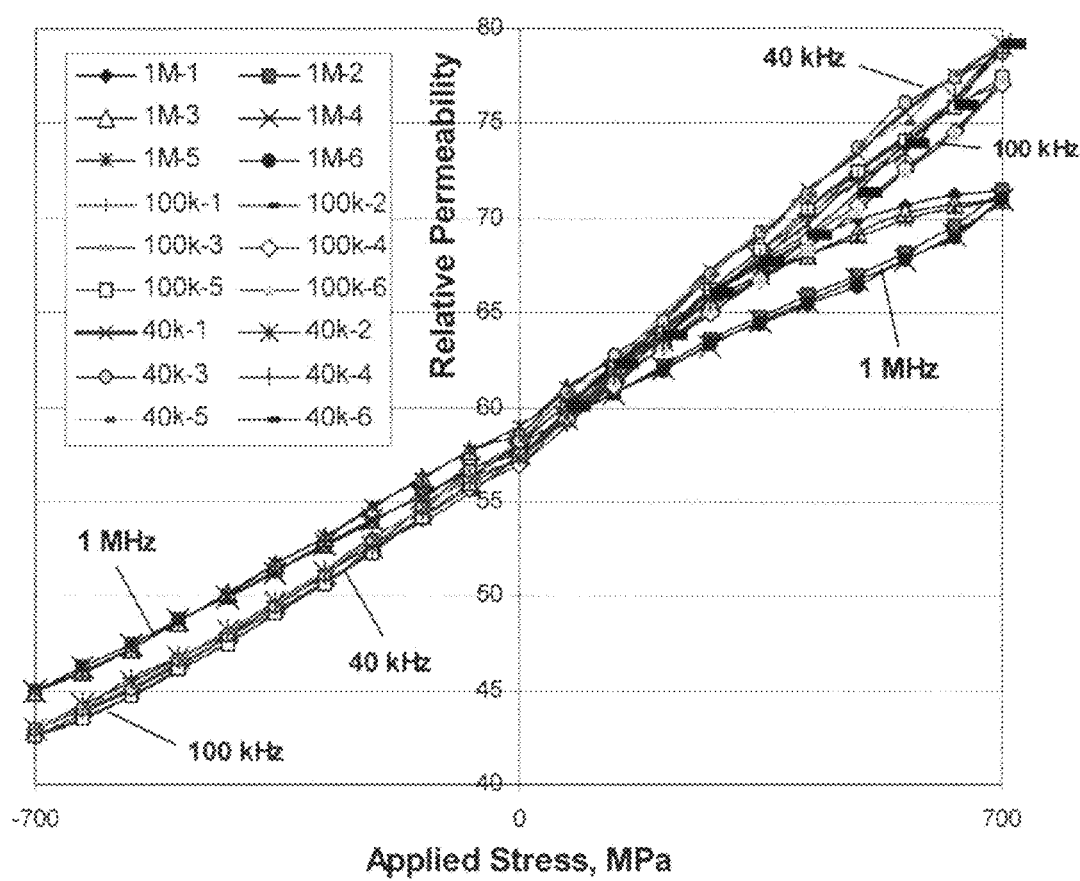
FIG. 11 shows the MWM measured magnetic permeability versus bending stress in a high-strength steel specimen at stresses from −700 to 700 MPa. The specimen was shot peened.

MWM permeability measurements on 300M high-strength steel specimens under fully reversed bending loading provide further indication of the capability of MWM sensors to perform stress measurements. The tests were performed on flat shot-peened specimens installed in a bending fixture. The stress range used in the test was between −700 MPa in compression and 700 MPa in tension. The stresses were determined from strains measured with a BLH strain gage using BLH instrumentation. The strain gages were attached to the "back" side. MWM magnetic permeability measurements were performed with the longer segments of the MWM drive winding perpendicular to the bending stress direction. In this orientation, the MWM measures permeability in the specimen longitudinal direction. FIG. 11 shows how the permeability measured at frequencies of 40 kHz, 100 kHz, and 1 MHz changes with applied bending stress. The data illustrate the sensitivity and quality of the permeability measurements for stress measurements in high strength steels over a wide range of stresses. The results clearly show the sensitivity of the MWM measurements to stress changes and reasonably small hysteresis, particularly in the compressive stress range.

The capability to perform directional permeability measurements allows characterization of both uniaxial and biaxial stresses, as described for example in U.S. patent application Ser. No. 10/351,978, filed Jan. 24, 2003, the entire teachings of which are incorporated herein by reference. In the latter case, the MWM permeability measurements at various sensor orientations reveal the directions of the principal stresses. Furthermore, permeability data from multifrequency MWM measurements can be used for reconstruction of stress distribution with depth. For typical excitation frequencies in the several kHz to several MHz range, the depth of penetration of the magnetic field is limited to a fairly thin layer near the surface, e.g., the first 0.5 mm (0.02 in.). However, lowering the excitation frequency, for example down to several Hz, and using alternative sensing elements such as magnetoresistive or giant magnetoresistive sensors, as described for example in U.S. patent application Ser. No. 10/045,650, filed Nov. 8, 2001, the entire teachings of which are incorporated herein by reference, permits measurements to a significantly greater depth. Also, MWM-Arrays allow imaging of stress distributions over wide areas.

The single layer designs of the drive and sensing elements supports low cost fabrication without introducing excessive requirements to align multiple layers. This significantly reduces manufacturing costs and increases the number of suppliers that can fabricate the sensors. However, to obtain reasonable signal to noise levels for such single turn coils (simple rectangles) at low frequencies, it is necessary to apply more current than is typical for conventional eddy current sensors, e.g., 1 A. One practical limitation on the sensing element size is fabrication costs (e.g., 75 µm line widths and larger are low cost with many suppliers, while smaller line widths is more costly and limits available suppliers). Another limitation is the relative contribution to the signal of the flux coupled by the active sensing area to the flux coupled by the relatively long leads. Thus, these leads are kept close together and the novel "flux cancellation" design is used to literally cancel the contribution from these long leads (thus instead of two conductors entering each sensing element, there are actually four conductors—two to sense the flux linked by the sensing elements and the leads themselves, and the other two to cancel the contribution from the leads, leaving just the response of the sensing elements).

Figure 12:
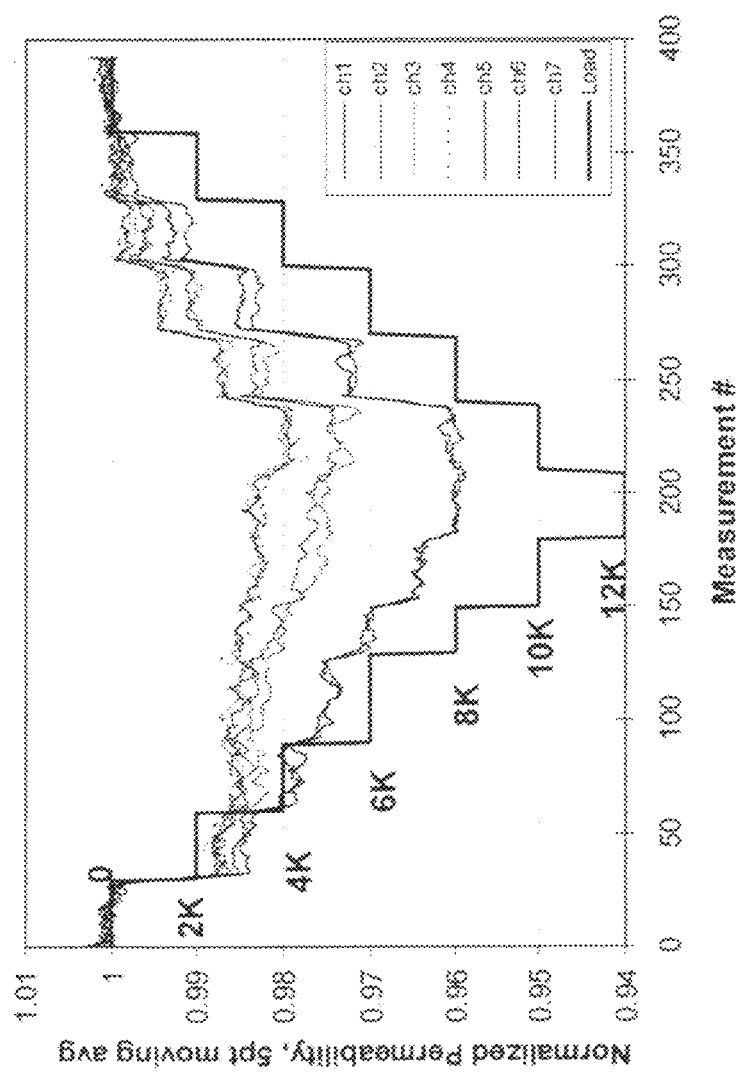
FIG. 12 shows MWM measured transverse permeability changes at incrementally increasing and decreasing tensile load (maximum load=53.4 kN (12,000 lbs); increment=8.9 kN (2,000 lbs)).
Figure 13:
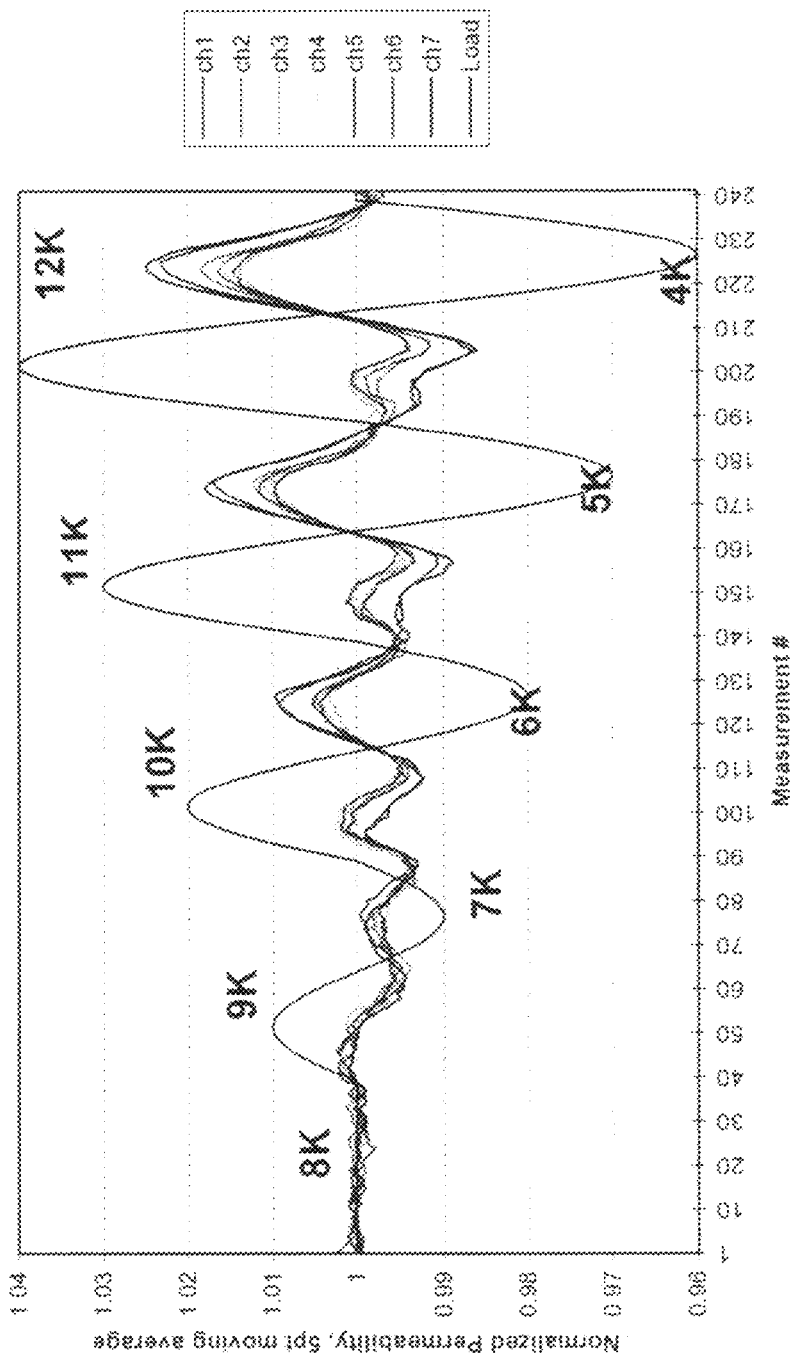
FIG. 13 shows a plot of MWM measured transverse permeability changes for a cyclically changing tensile load.

FIG. 12 shows the results of another set of tests illustrating the magnetic permeability changes due to the Poisson's effect or the transverse contraction under tensile axial load. A 7-channel MWM-Array was mounted on the specimen with the longer segments of the MWM-Array drive oriented along the specimen axis, i.e., parallel to tensile load orientation during tests, so that the magnetic permeability in the transverse direction is measured. In this test, the tensile load was first incrementally increased by 8.9 kN (2,000 lbs) to the maximum tensile load of 53.4 kN (12,000 lbs) and then incrementally decreased to 0. The estimated maximum axial stress in the center of the area was about 700 MPa (100 ksi). After each load increment, a constant load was maintained for a period of time. The loading pattern and MWM-Array measured transverse permeability in all seven channels is shown in FIG. 12. The observed change in MWM-Array measured transverse permeability appears to mimic changes in transverse strain. The lowest permeability changes occur near the center. The results emphasize the importance of permeability measurements and suggest that bidirectional permeability measurements are critical to stress measurements even under uniaxial loading. Similar results are obtained with the cyclic loading pattern of FIG. 13, which had a mean load of 8,000 lbs and load amplitude progressively increasing from 1,000 lbs (load range of 2,000 lbs) to 4,000 lbs (load range of 8,000 lbs).

The ability to detect and image stress distributions has implications for the detection and imaging of early stage fatigue damage as well. Fatigue tests of 4340 steel specimens revealed the capability to detect precrack damage early in the fatigue life. These specimens were designed with a cylindrical cavity in the gage section, where an MWM-Array could be mounted, and reinforcement ribs on the back side. This provides a nonuniform stress distribution with the maximum stress in the central portion of the cavity, as verified by a finite element analysis, beneath the footprint of the MWM-Array. The shape and stress distribution within the cylindrical cavity can be varied to simulate the geometry of high strength steel components of interest. In one embodiment MWM or MWM-Array sensors are oriented with their longer winding segments aligned parallel or perpendicular to the direction of likely fatigue crack orientation. The sensor aligned perpendicular to this direction is most sensitive to fatigue damage and crack monitoring, while the sensor with longer drive segments parallel to this direction is most sensitive to stress (i.e., magnetic permeability is measured dominantly in the direction perpendicular to the longer drive segments, while conductivity, or induced current flow, is sensed dominantly parallel to the direction or the longer winding segments). In another embodiment, multiple series connected or multiplexed eddy current sensors, such as MWM-Arrays, are mounted at selected critical and non critical locations to support both fatigue and stress monitoring either continuously or periodically or on a scheduled or unscheduled basis depending on convenience or loading/fatigue/overload events.

In another embodiment, MWM-Arrays we used in a surface mounted or even non contact (where lift-off is measured using grid methods) to monitor stress and proximity (or vibrations). As with strain gages or extensometers this information can be used to control load frames, monitor changes in material properties or structures, or monitor in service behavior and damage. Integration of information with that from strain gages or extensometers can be used to support decisions regarding fitness for service, material life or to assess material performance in fatigue tests. Combination with new fiber optic strain gages is also useful.

Figure 14:
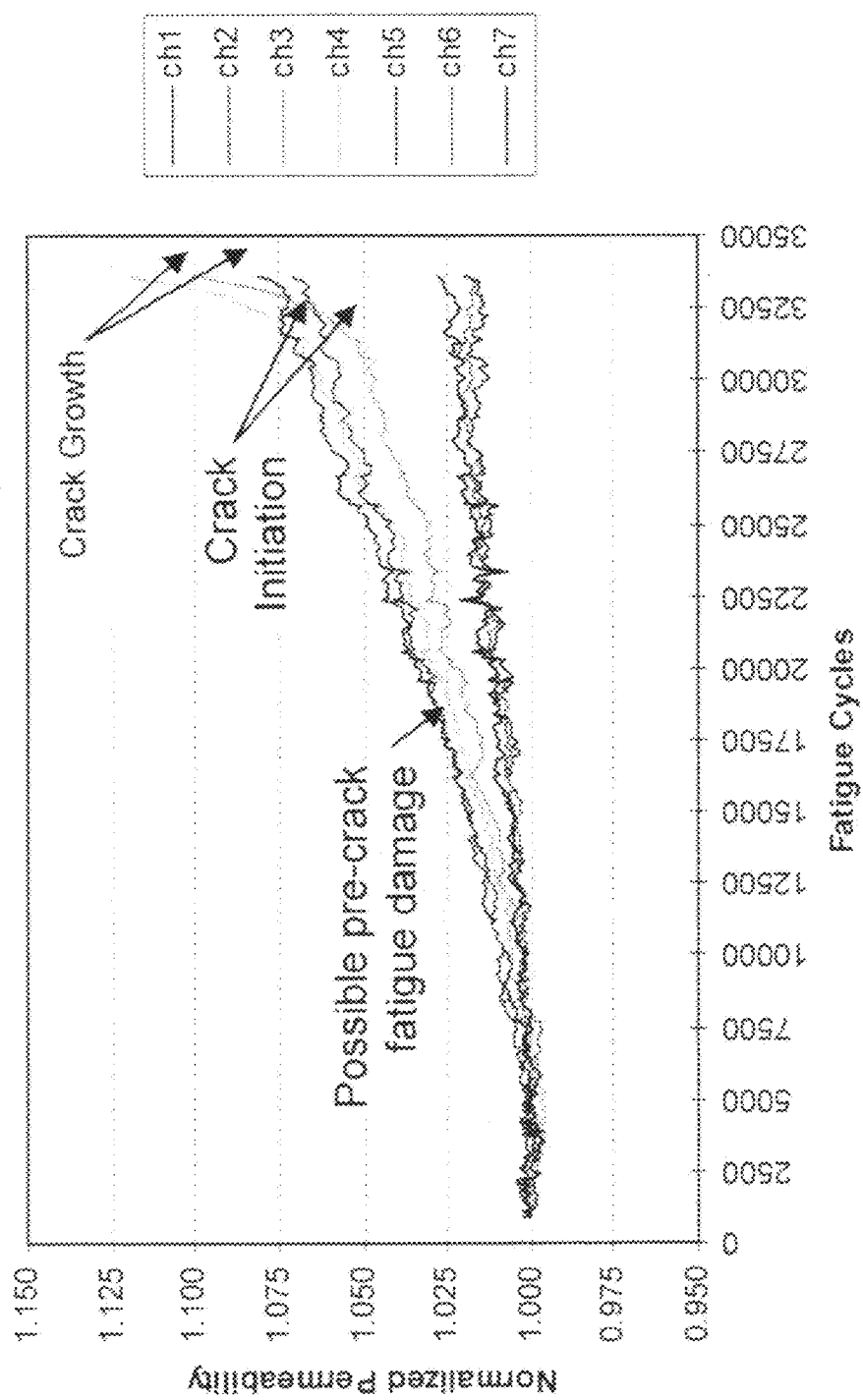
FIG. 14 shows a plot of normalized permeability against the number of fatigue cycles for a shot peened 4340 steel specimen.

FIG. 14 shows the permeability changes during a test using a 7-channel MWM-Array. There is virtually no change in the measured permeability up to 7,000 cycles. The change in the slope of MWM measured permeability in the four centrally located channels at about 7,000 cycles is most likely associated with residual stress relaxation and precrack fatigue damage. This fatigue damage stage extends, perhaps, up to 17,000 cycles followed by initiation and extension of multiple microcracks. Two of the channels show a significant permeability increase at 32,000 cycles indicating coalescence of closely spaced cracks and faster crack growth. SEM analysis on this specimen revealed a few small cracks, with the longest crack approximately 200 ÿm (0.008 in.) long. This crack was also confirmed by fluorescent liquid penetrant inspection (FPI). The FPI indication appeared as a tiny "speck" judged to be on the order of 0.25-mm (0.01-in.) long.

Figure 15:
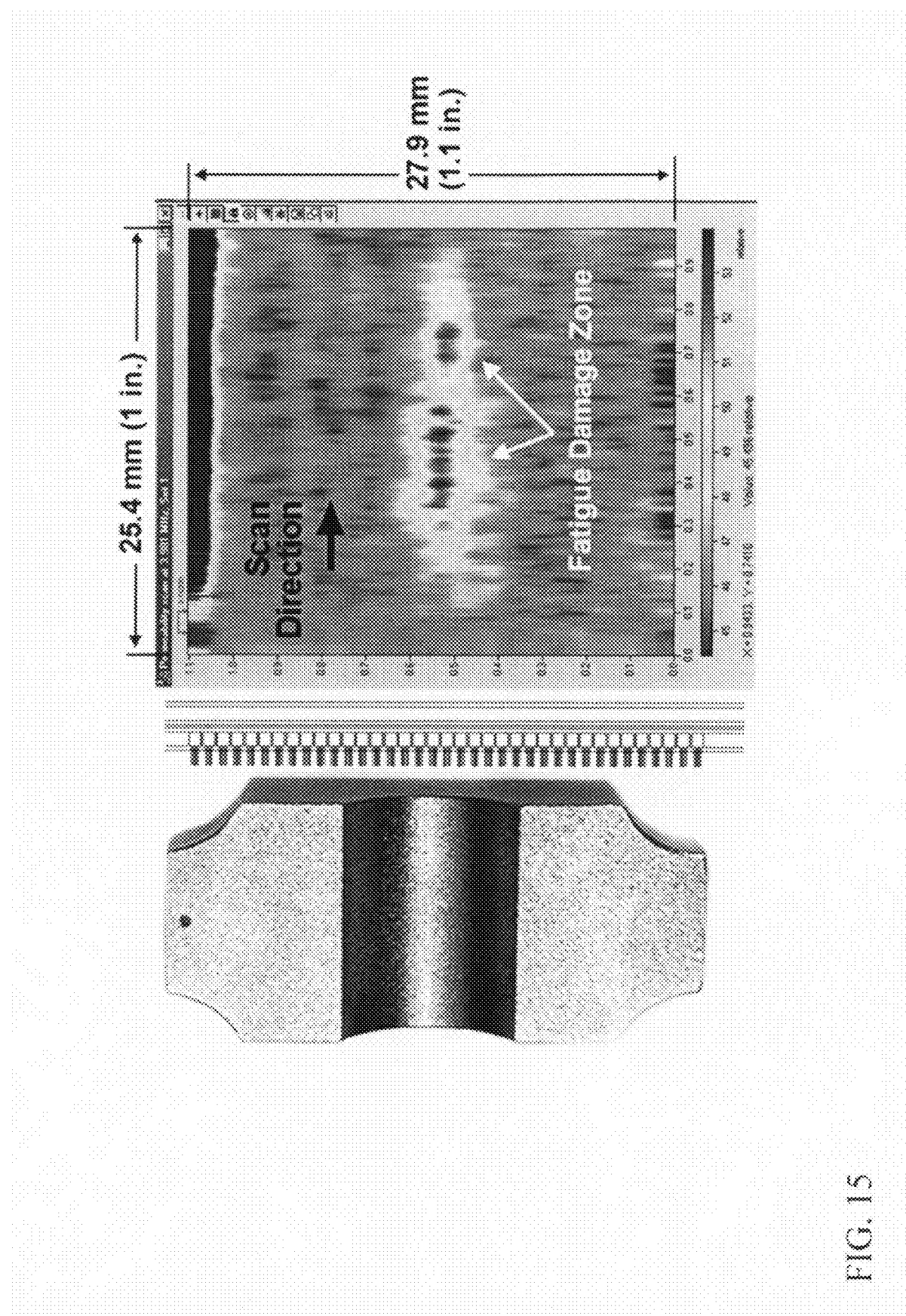
FIG. 15 shows an image of the MWM measured permeability of the fatigue damage zone at the end of the fatigue test.

The fatigue critical area of this specimen was also scanned with an imaging MWM-Array, with the drive oriented perpendicular to the axis of the coupon cavity. This orientation is perpendicular to anticipated predominant orientation of fatigue cracks, and is the same as in fatigue test monitoring of FIG. 14. FIG. 15 shows a permeability image and aligned intermittent regions of increased permeability having a combined length of about 20 mm (0.75-in.) Three of these regions appear to contain short indications characterized by the highest measured permeability. The other relatively high permeability regions are likely to indicate stress relaxation due to the cyclic loading and fatigue damage prior to formation of detectable cracks. These regions of enhanced permeability are also consistent with the higher stress region of the component from the finite element analysis.

Figure 16:
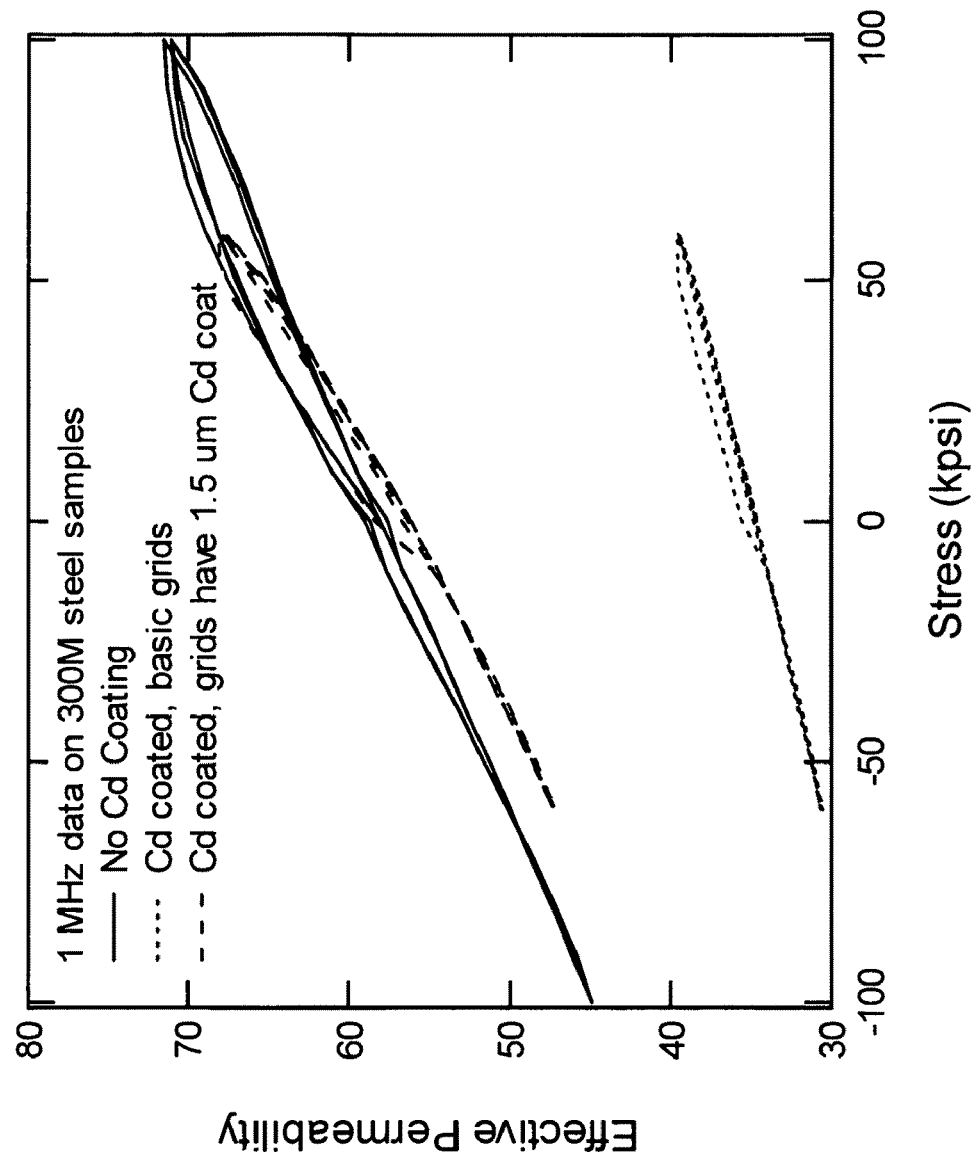
FIG. 16 shows the effective permeability variation with applied stress for coated and uncoated samples.

For cadmium-plated high-strength steel components, it is important to account for the effect of the cadmium layer on the MWM measurements. This is illustrated in FIG. 16, where a coating model was applied to the multiple frequency data obtained from MWM measurements on the 300M high strength steel specimens. Qualitatively, this data (from 39.8 kHz to 1 MHz) showed a decrease in the effective permeability and lift-off compared to measurements on the uncoated specimen. This is consistent with the presence of a nonmagnetic conducting surface layer on magnetizable substrate. The model assumed a Cd layer (electrical conductivity of 22% IACS, 12.76 MS/m) on top of a magnetizable substrate (electrical conductivity of 3.4% IACS, 2 MS/m), so that the unknowns in this model were the lift-off, Cd layer thickness, and permeability of the substrate (steel). The stress distribution, and hence the magnetic permeability, is not necessarily uniform with depth into the substrate and definitely not uniform for a shot peened steel. As the first step, the thickness of the Cd layer on an unstressed sample was estimated using a least-squares minimization routine on the multiple frequency data. In another embodiment a fast table lookup within a lattice is used. Assuming a substrate permeability of 57.1, the Cd thickness was estimate to be 1.5 ÿm. Using this thickness, substrate permeability/lift-off grids were then generated so that the effective permeability of the substrate could be determined. FIG. 16 shows permeability vs. stress curves for non-plated steel, for Cd-plated steel using a model that does not account for the Cd layer, and for Cd-plated steel using a model that does account for the Cd layer. As shown in FIG. 16, using grids that have a thin Cd layer can provide estimates of the permeability that are similar between the coated and uncoated samples. Without this compensation for the presence of the Cd coating, the permeability estimates are significantly reduced for the coated sample.

The numerical value for the Cd layer thickness of 1.5 µm is small compared to the nominal thickness of 10-20 µm because of the assumed conductivity for the layer. For these relatively thin layers and intermediate excitation frequencies, the measurements are essentially sensitive to the product of the layer thickness and electrical conductivity. For alloy layers (e.g., cadmium-titanium alloys) or for microstructural variations due, for example, from porosity introduced during the coating process, the electrical conductivity can be lower, in the range of 1.2-7.0 MS/m (2-12% IACS) and the corresponding thickness larger. The thicker Cd layer values can be accommodated, without appreciably affecting the permeability estimates, if a lower conductivity is used for the Cd layer.

The properties of the coating material layer and even the base material itself can be obtained from multiple parameter estimation approaches. The use of multiple frequencies allows more than two parameters to be estimated. As an example, three, four and five parameter estimation routines have been developed for determining the properties of coatings, such as MCrAlY coatings used on turbine blades and vanes. As described in more detail in the DOE Phase II proposal "Intelligent Probes for Enhanced Non-Destructive Determination of Degradation in Hot-Gas-Path Components," the entire teachings of which are incorporated herein by reference, a four parameter estimation routine is used for determining the coating electrical conductivity and thickness, the sensor lift-off, and the substrate electrical conductivity for nonmagnetizable materials. A five parameter algorithm that allows determination of an additional parameter, e.g., magnetic permeability when one of the layers is magnetizable is also described. Clearly, this multiple parameter estimation approach can be applied to different combinations of electrical and geometric properties for the various layers. This also applies to shot peened materials or materials with a degraded near-surface layer. For example, it was successfully demonstrated for turbine blades with two types of coatings. Since the processing time typically increases as the number of properties to be estimated increases, this approach for determining the layer and substrate properties can be performed prior to continuous stress measurements so that simpler models or measurement grids can be used while the measurements are being performed. For example, this can involve characterizing the coating thickness and conductivity using the multiple parameter algorithm, using this information to generate substrate permeability-lift-off grids, and then performing the continuous stress measurements. Alternatively, rapid table look up in lattices or hypercubes can be performed.

Measurements can also be performed while the hydrogen embrittlement occurs. As an example, cathodic charging was used to introduce hydrogen into the steel using a setup similar to some previously described [Grendahl, 2002]. Here, a flat 4340 steel specimen is placed in the bending fixture with a 0.4-liter vessel with a 25 mm hole in the bottom mounted and sealed on the top of the 4340 steel specimen. The specimen is loaded to stresses as high as 150 ksi. A strain gage mounted to the compressive side of the specimen provides an independent measure of the strain so the bending stresses during loading and cathodic charging may be monitored. After loading to the desired stress level, the permeability is measured until an initial transient period passes. Then approximately 0.3 liters of a 3.5% NaCl solution is poured into the vessel. An electrochemical cell is formed with the 4340 specimen as the working electrode. A graphite rod serves as the counter electrode and a standard calomel electrode (SCE) provides a reference point for the electrochemical potential. The working electrode, counter electrode, and SCE were connected to a Schlumberger SI 1286 potentiostat and a selected potential between −1.15 V and −1.25 V was applied to effect cathodic charging. Magnetic permeability measurements with an MWM-Array can be performed in either scanning mode or with a permanently mounted MWM-Array, on the exposed (tension) side of the test specimen. This type of in-process monitoring can be performed for other processes that include material property changes.

Figure 17:
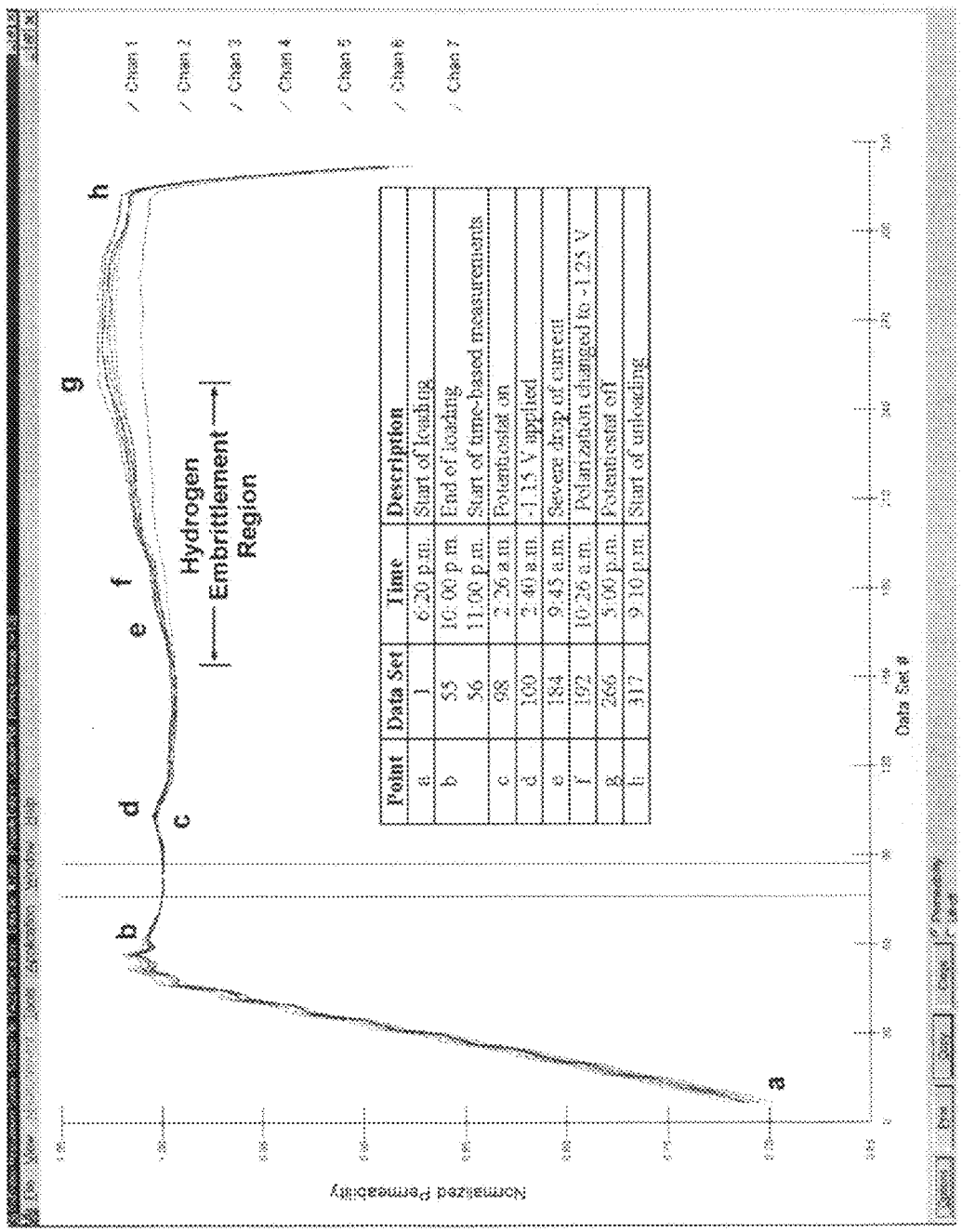
FIG. 17 shows MWM-Array measured permeability changes during the complete loading/hydrogen exposure/unloading test cycle.

FIG. 17 shows MWM-Array measured permeability changes during the complete test cycle for one specimen. The normalized permeability measurements were made with the 7-channel MWM-Array attached on the tension side of the specimen. In this test, the specimen was first monitored with the mounted MWM-Array before a bending load was applied to the specimen. Then, the specimen was loaded in bending to 700 MPa (100 ksi) stress level as measured with a strain gage. The MWM-Array measured permeability increased due to the stress from point a to point b. Between points b and c, the specimen was monitored by the MWM-Array at the constant stress level. Then, at point c, the vessel was filled with 3.5% NaCl solution, the initial open circuit potential was measured, adjustments made, and −1.15 V potential (relative to the standard calomel reference electrode) was applied at point d. After an initial period of a fairly stable magnetic permeability between sets 120 and 160, i.e., for about three hours, a distinct and steady increase in the MWM-Array measured permeability was observed for the next nine hours, i.e., up to the time when polarization was discontinued (up to point g). Note that the potential was changed to −1.25 V at point f. Between points g and h, the stress was maintained, while there was no applied potential. Finally at point h, the specimen unloading started.

Example sensor arrays are the MWM-Arrays shown in FIG. 2 through FIG. 5, although other array formats can also be used, such as those described in U.S. patent application Ser. Nos. 09/666,879 and 09/666,524. These applications also describe using a magnetic material in combination with the sensor as a load cell and adjusting the sensitivity of the response through the selection of the type and dimensions of the material. Alternatively, if the changes in the stress distribution occur relatively slowly, periodic measurement of the stress distribution can be performed. This can be accomplished with occasional measurements with an MWM-Array that has been mounted to a surface or by scanning eddy-current sensing arrays over the surface to provide a complete mapping of the material properties over the entire surface. In addition, measurements in multiple orientations, preferably two orthogonal orientations, can be performed to determine anisotropic material property variations associated with changes in stresses in the fasteners and can be determined with directional eddy-current sensor arrays. The MWM-Array is one such example as the sensing elements respond preferentially to the magnetic permeability oriented perpendicular to the extended segments comprising the primary winding. In another embodiment the larger drive segments are oriented at an angle, e.g., 45 degrees, relative to the scan direction. If cracks are likely to form in the direction perpendicular to the scan direction, then this is necessary to increase sensitivity to crack size or precrack damage.

In another embodiment an array is configured in an x or v so that two drive orientations are provided in as two or one layer respectively. An example of this configuration is described in U.S. patent application Ser. No. 10/419,702, filed Apr. 18, 2003, the entire teachings of which are incorporated herein by reference. In one embodiment the legs of the v or x are at different angles relative to the scan direction (or the x or v is rotated relative to the scan direction) so that cracks respond differently and material variations that are isotropic respond the same. This improves discrimination capability. This can also be used for buried object imaging.

Conventional eddy-current designs are not ideal for permanent mounting. Conventional eddy-current techniques require varying the proximity of the sensor (or lift-off) to the test material or reference part by rocking the sensor back and forth or scanning across a surface to configure the equipment settings and display. For example, for crack detection the lift-off variations are generally displayed as a horizontal line, running from right to left, so that cracks or other material property variations appear on the vertical axis. Affixing or mounting the sensors against a test surface precludes this calibration routine. The probe-to-probe variability of conventional eddy-current sensors prevents calibrating with one sensor and then reconnecting the instrumentation to a second (e.g., mounted) sensor for the test material measurements. These shortcomings are overcome with conformable eddy-current sensors that provide absolute property measurements and are reproduced reliably using micro-fabrication techniques. Calibrations can also be performed with duplicate spatially periodic field sensors using the response in air or on reference parts, which may simply be different areas of the same component, prior to making the connection with the surface mounted sensor. The capability to characterize fatigue damage in structural materials, along with the continuous monitoring of crack initiation and growth, has been demonstrated, as described in U.S. patent application Ser. Nos. 09/666,879, 09/666,524, and 10/102,620. This inspection capability is suitable for on-line fatigue tests for coupons and complex components, as well as for monitoring of difficult-to-access locations on both military and commercial aircraft. In another embodiment, mounted sensors are removed to perform other examinations (e.g., acetate replicas to defect small cracks), and must be reattached using a reference calibration to the previously recorded value. By recalibrating the sensor with the same values as before removal, then the continuation of monitoring will begin with the same values, e.g., permeability, as before the sensor was removed and reinstalled.

Another aspect of this embodiment of the invention is the inspection of nickel alloy engine materials, such as Alloy 738 or Alloy 718, where shot peening and/or heat treatment may produce near surface relative permeability greater than 1.0. This is also described in U.S. patent application Ser. No. 10/419,702. Higher permeability regions are typically created near the surface by the shot peening and/or heat treatment process. At sufficiently high frequencies, the magnetic field is confined near the surface of the MUT and reflects only the permeability (and stress) of the surface region. At lower frequencies, the magnetic field can penetrate through this region and the average or effective permeability is reduced. At sufficiently low frequencies, the magnetic field penetrates far enough into the base material that the permeability approaches 1.0. High resolution images of permeability can then be used to map residual stress variations to qualify shot peening or other manufacturing processes or to assess material aging/material degradation, as described in more detail in U.S. patent application Ser. No. 10/351,978. Then, regions with unacceptable residual stresses might be reworked (e.g., blending and reshot peening) to extend life.

Another aspect of this embodiment of the invention relates to the application of a stress-sensitive material to a test material and monitoring the properties of this stress-sensitive material to infer the stress distribution or mechanical load on the test article. The stress sensitive material could be a magnetic material in which the magnetic permeability changes significantly with stress, as illustrated in FIG. 11. An alternative stress-sensitive material is one whose electrical conductivity changes significantly with stress. Also, different layers with different sensitivity might be used, for example some layers with permeability being sensitive, and other layers with conductivity being sensitive. These materials could be magnetic or nonmagnetic. In general, according to the literature on strain gages, metals typically have a gage factor reflecting change in resistance per unit strain of between 2 and 4. Representative values are listed in Table 1. Preferable materials for nonmagnetic stress-sensitive materials are platinum and platinum alloys because of the relatively large gage factors. It should be noted that conductivity variation with strain tends to become nonlinear for large strains and the listed gage factors are most applicable to situations of low strains. The choice of the stress-sensitive material can therefore depend on the strains anticipated for the inspection.

TABLE 1

Gage factors for stress-sensitive conducting materials.

| Material | Composition | Gage Factor |
| --- | --- | --- |
| Platinum | 100% Pt | 6.1 |
| Platinum-Iridium | 95% Pt, 5% Ir | 5.1 |
| Platinum-Tungsten | 92% Pt, 8% W | 4.0 |
| Isoelastic | 55.5% Fe, 36% Ni, 8% Cr, 0.5% Mo | 3.6 |
| Karma | 74% Ni, 20% Cr, 3% Al, 3% Fe | 2.4 |
| Constantan | 55% Cu, 45% Ni | 2.0 |
| Nichrome | 80% Ni, 20% Cu | 2.0 |
| Monel | 67% Ni, 33% Cu | 1.9 |
| Manganin | 84% Cu, 12% Mn, 4% Ni | 0.47 |
| Nickel | 100% Ni | −12.1 |

Figure 18:
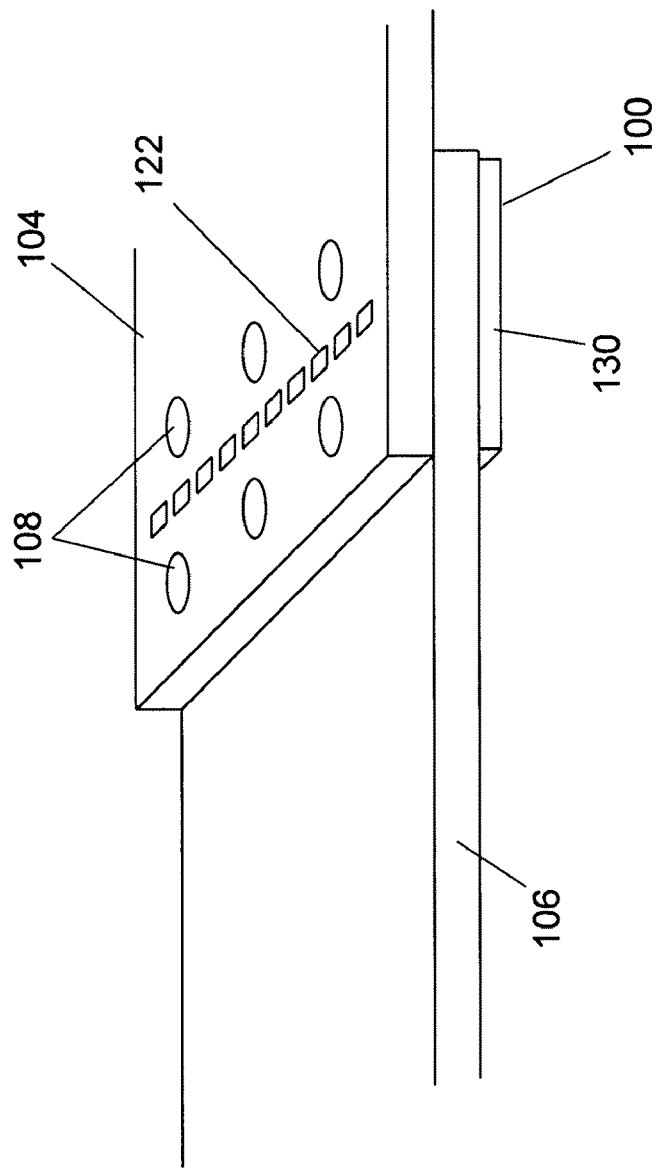
FIG. 18 shows an illustration of a lap joint with a stress-sensitive material and a sensor array.
Figure 19:
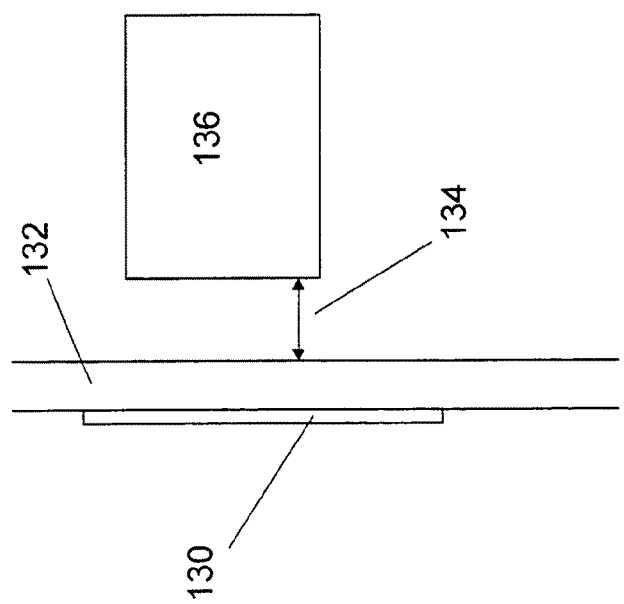
FIG. 19 shows an illustration of a non-contact measurement of a stress-sensitive material.

Monitoring the properties of a stress-sensitive material attached to a test material is most useful in situations where direct nondestructive measurements of the stresses in the test material are relatively difficult, such as in aluminum with eddy-current sensors. In contrast, monitoring the permeability changes of a layer of magnetic material or electrical conductivity changes of a layer of stress-sensitive non-magnetic material integrally attached to the test article can offer substantially greater sensitivity. The properties of the attached layer material can be monitored using a permanently mounted sensor or with a scanning sensor array to create images of the stress distribution. An illustration of this approach is given in FIG. 18, where the stress-sensitive material 130 is affixed to the back of the lap joint 100, which has layers 104 and 106 joined by fasteners 108. The sensing elements 122 are shown in a linear array, but they could also be distributed among and around the fasteners as well. In this case, the drive winding is not shown. The measurements can also be performed in a non-contact fashion, as shown in FIG. 19, where an air gap 134 is maintained between the sensor or sensor array 136 and the test material 132. In both FIG. 18 and FIG. 19, the magnetic fields generated by the eddy-current sensor are projected through the test material so that the remote fields interact with the attached stress-sensitive layer and the sensor and attached layer material effectively operate as a load cell. In one embodiment, stress sensitive materials (or materials more sensitive to other affects such as temperature) might be located on the near and far side of a layer or at multiple depths within a multiple layered construct. Also, as described latex strips, composites or other directionally sensitive media might be used to measure stress in different directions or to simply aid in differentiating between affects at different depths.

The sensitivity of this measurement approach is affected by the electrical and geometric properties of the stress-sensitive layer attached to the test material. The material should be selected so that the permeability or conductivity change for an anticipated stress level is detectable with the sensor and instrumentation. Furthermore, the material should be relatively thin to better reflect the stress distribution of the test material. However, it should also be thick enough to provide a measurable signal with the sensor or sensor array. Selection of the thickness of the layer must therefore balance these competing effects. The magnetic or non-magnetic stress-sensitive material can also be applied to the surface of the test material near the sensor.

The properties of the stress-sensitive material and even the base material itself that the coating is applied to can be obtained from multiple parameter estimation approaches. The use of multiple frequencies allows more than two parameters to be estimated. As an example, three, four and five parameter estimation routines have been developed for determining the properties of coatings, such as MCrAlY coatings used on turbine blades and vanes, as described above.

This type of state sensitive material layer could also be applied other inspection or monitoring applications. Instead of stress, the sensitive layer may have a greater temperature sensitivity so that the temperature of the material can be monitored. It may also permit the detection and characterization of thermal or mechanical overload events that can compromise the future use of the article.

As another alternative embodiment, in addition to inductive coils, other types of sensing elements, such as Hall effect sensors, magnetoresistive sensors, SQUIDS, and giant magnetoresistive (GMR) sensors, can also be used for the measurements. The use of GMR sensors for characterization of materials is described in more detail in U.S. patent application Ser. No. 10/045,650. While conventional eddy-current sensors are effective at examining near surface properties of materials, but have a limited capability to examine material property variations deep within a material. GMR sensors respond to magnetic fields directly, rather than through an induced response on sensing coils, which permits operation at low frequencies, even DC, and deep penetration of the magnetic fields into the test material. The GMR sensors can be used in place of sensing coils, conventional eddy-current drive coils, or sensor arrays. Thus, the GMR-based sensors can be considered an extension of conventional eddy-current technology that provides a greater depth of sensitivity to hidden features and are not deleteriously affected by the presence of hidden air gaps or delaminations. In an alternative embodiment electric field sensors, IDEDs described in U.S. Pat. Nos. 4,814,690 and 6,380,747 and in U.S. patent application Ser. No. 10/040,797, filed Jan. 7, 2002, and Ser. No. 10/225,406, filed Aug. 20, 2002, the entire teachings of which are hereby incorporated by reference might be used to monitor stress or temperature, moisture content or contamination or overload of fatigue in adhesives, epoxies, glass, oil, plastics and in single or multiple layered media. Here the conductivity and dielectric constant or complex permittivity and layer thicknesses are measured using the same methods as for magnetic field sensing. In one such electric field method multiple layers of material are added on top of a sensor each sensitive to different chemicals or biological materials. In another embodiment coatings on pharmaceuticals are characterized for manufactured quality, such as density, moisture content or density of suspended particles in a time release coating.

There are a variety of inspection applications that could take advantage of the capabilities of a GMR-based sensing technology. One is the imaging of damage, such as cracks, inclusions, and corrosion, deep below the surface of conducting materials typically found in aging aircraft. These measurements can also be performed on magnetic materials where the skin depth is relatively small when conventional eddy-current technology and excitation frequencies are used. Since the GMR sensor responds to magnetic field variation and the magnetic field created by a drive coil or primary winding can readily penetrate air gaps, these sensors can be used for non-contact and remote measurements where air-gaps are present between conducting and/or magnetic material layers. For example, measurements of the electrical properties, such as the electrical conductivity or magnetic permeability, of inaccessible materials can be used with correlation curves to assess the temperature or stress of the hidden materials. As an example, the use of direct temperature measurements for characterizing the thermal response of inaccessible surfaces is considered an ill-posed inverse heat conduction problem. In contrast, low-frequency magnetic fields can penetrate the test materials to inspect the remote surface with simultaneous measurements at higher frequencies used to compensate for near-surface property variations. This new capability may be suitable for health monitoring for engines. An example is the monitoring of internal temperatures in aircraft engines, for example, in the compressor or turbine stages. This technology may also be suitable for the non-contact remote monitoring of stresses in ferrous materials, such as landing gear after a hard landing or for monitoring the stresses on steel bolt in an aluminum structure through the aluminum at relatively low frequencies or even at DC or in other steel structures.

Figure 20:
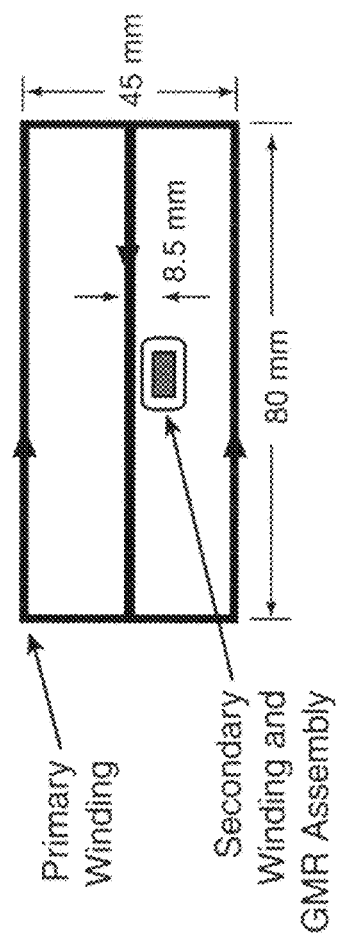
FIG. 20 shows a layout for a single turn Cartesian geometry GMR magnetomer.
Figure 21:
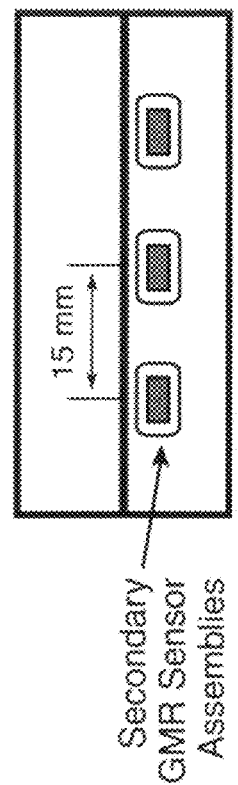
FIG. 21 shows a layout for a multi-element GMR array.

GMR-based magnetometers can be incorporated into a variety of primary winding geometries, such as rectangular, circular, or elliptical coils. An example rectangular or Cartesian-geometry GMR-based magnetometer is illustrated in FIG. 20. A GMR array is shown in FIG. 21. The parallel primary windings are laid out in a fashion similar to the MWM-Array designs, which has shown advantages in the generation of C-scan images.

The winding layout of FIG. 20 allows the relative polarity of the two constituent current loops to be changed to generate a structure with twice the effective wavelength. This permits inspection at two different depths, at a single frequency. For the results presented here, the currents were directed as shown, with the center leg of the winding carrying twice the current of the two edge (or return) windings. The two half-wavelength current loops have identical areas and oppositely directed currents of equal magnitude, so that their effective dipole moments cancel out, resulting in no net dipole moment in the far field. Here the dominant far-field moment is a quadrupole. This elimination of the net dipole moment of the sensor improves measurement reliability because it reduces the sensitivity of the magnetometer to objects outside its nominal range of sensitivity.

The GMR sensing element requires biasing with a constant magnetic field. To provide this bias, and to address the high nonlinearity of the sensor's transfer characteristic, it is placed in a feedback configuration with a secondary biasing coil. In this way, the magnetic field at the GMR sensor remains nearly constant during operation, eliminating the effect of the non-linear transfer characteristic, while maintaining sensitivity at low frequencies. The magnitude of the current in the secondary winding is taken as the output signal, and since the relationship between this current and the magnetic field for an air-core winding is perfectly linear, so is the transfer characteristic of the entire hybrid sensor structure.

Figure 22:
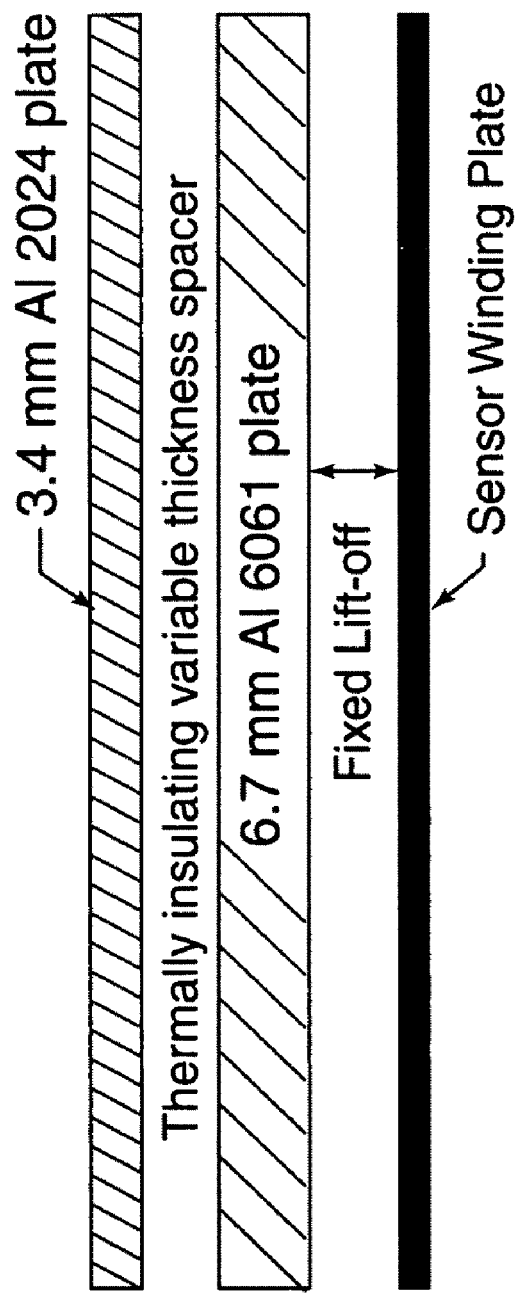
FIG. 22 shows a schematic for remotely monitoring the temperature of a plate.
Figure 23:
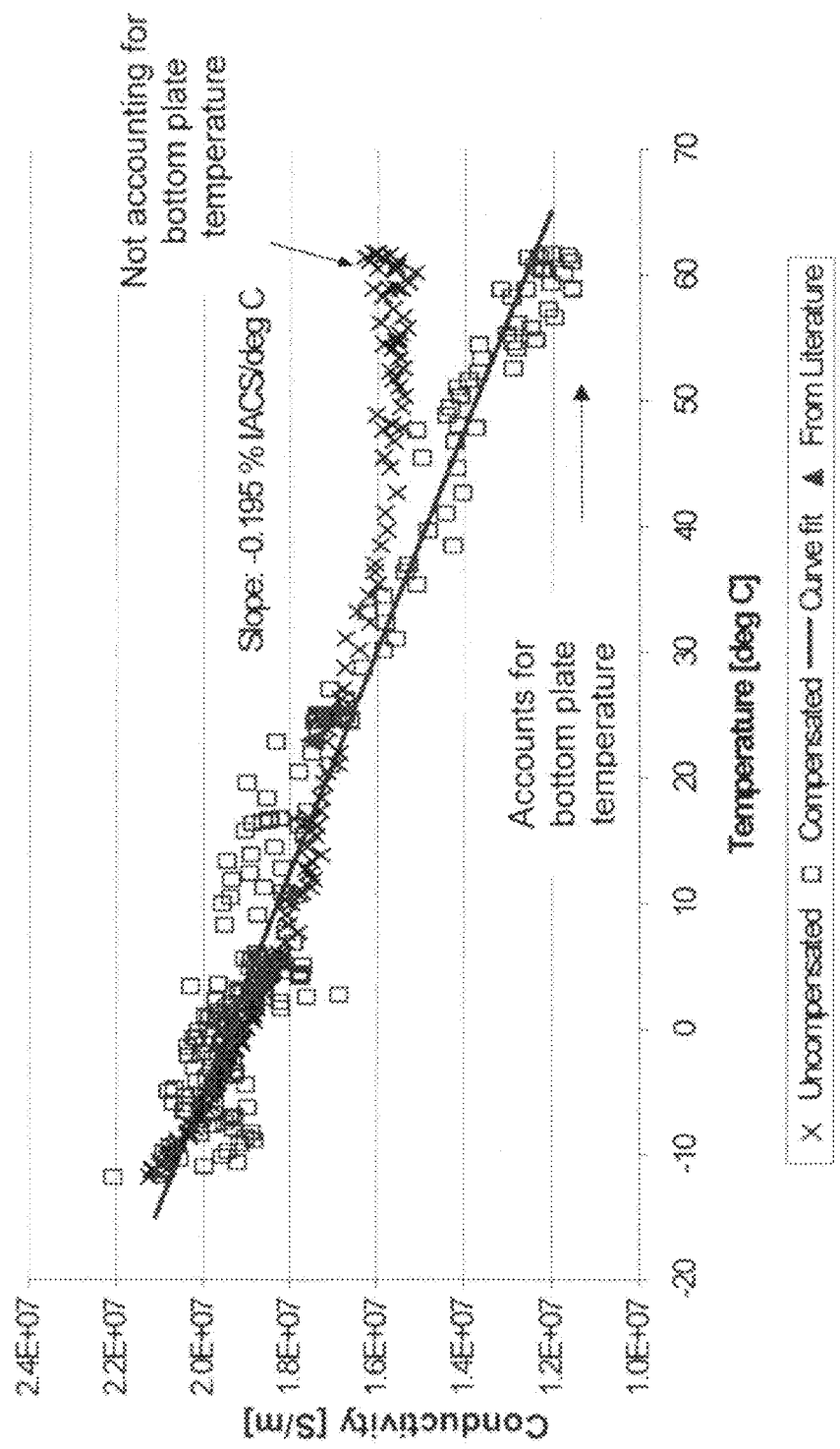
FIG. 23 shows the top plate conductivity as a function of temperature with and without compensation for changes in the conductivity of the bottom plate, which is between the top plate and the sensor.

One example application using a GMR sensor is for monitoring properties through intermediate layers of metal. In this case, the absolute electrical properties are measured through thick metal plates and then related to other physical properties of interest. FIG. 22 shows one such layered geometry, with a low frequency (100 Hz) measurement used to remotely monitor the temperature dependent conductivity variation of an aluminum plate through a 0.25-in. thick aluminum plate. The thickness of the upper plate (remote from the sensor), the conductivity and thickness of the bottom plate (near the sensor), as well as its lift-off (proximity) from the sensor windings, are incorporated in the model used to generate the appropriate measurement grids. The two unknown properties are the conductivity of the upper plate and the thickness of the thermally insulating nonconducting spacer between the two plates, which also varied significantly with the temperature of the upper plate. The ability to measure the two unknown parameters independently is demonstrated by taking measurements at room temperature with spacers of varying thickness and demonstrating that the data follow a constant-conductivity line in the grid. To verify and record the actual plate temperatures, thermocouples were attached to both metal plates. The top plate was initially chilled and then gradually heated with a hot air gun. The data of FIG. 23 shows that both the conductivity and spacer thickness are affected by the plate temperature.

In this experiment, the temperature of the bottom plate also increased, despite the thermal insulation. Ignoring this effect yields the plot in FIG. 23 with cross symbols. To compensate for the temperature variation of the bottom plate, data were also taken at 10 kHz simultaneous with the 100 Hz measurement. At this higher frequency the bottom plate appears infinitely thick since it is more than several skin depths thick and a simple conductivity/lift-off grid can be used to independently determine the bottom plate's conductivity. Once this value is obtained, it can be used in the estimation of the upper plate conductivity via a three-dimensional measurement grid, called a grid lattice. Using this method, the data shown with squares in FIG. 23 are obtained. As expected, it follows a linear relationship. Example applications of such remote temperature and stress measurement include: 1) measuring temperature of carbon fibers in an epoxy matrix, 2) measuring stress or temperature on fibers in a composite where the fibers are coated with a magnetic or other material that can be sensed using magnetic or electric fields, 3) measuring temperature on the outside of a wing or other cavity from the inside using sensors mounted on the inside with or without an added more sensitive on the outside of the metal (or other material) layers, 4) measuring stress on a bearing race at the outside diameter (or rolling surface) from the inside diameter or using an embedded sensor, 5) measuring stress or temperature as a function of depth, 6) measuring stress or temperature variations with time and/or space near an internal geometric feature such as a cooling hole or at the inlet of an aircraft engine.

Figure 24:
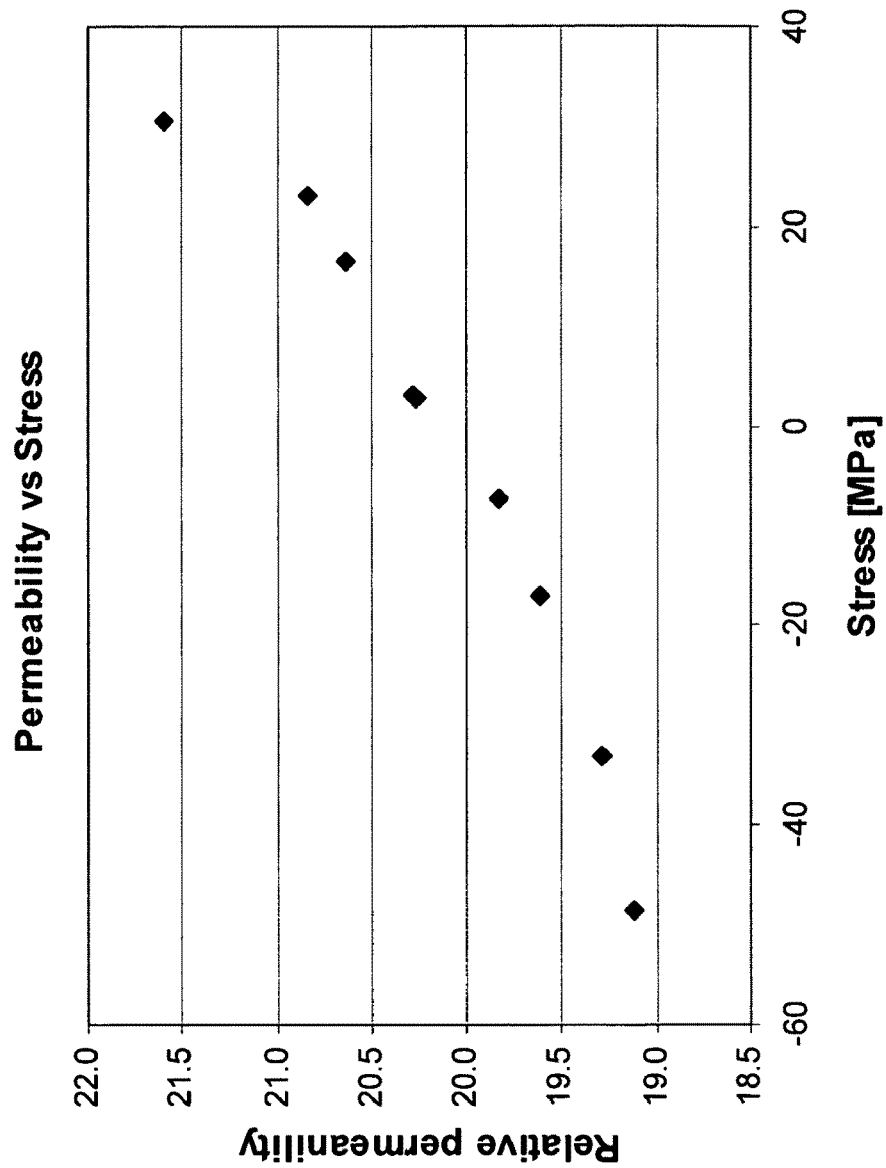
FIG. 24 shows a plot of the top plate relative permeability as a function of the top plate strain at varying levels of applied stress.

Another example of demonstrated measurements with a GMR sensor is the monitoring of stress. In this case, measurements were performed on a hidden steel layer in a thick structure. A 1.4 mm thick steel plate was suspended over a 6.7 mm Al 6061 plate using a 3 mm thick spacer located in the center. A 5 kg weight was used to keep the center part of the plate from moving. The measurement grid used in this case was a permeability/spacer thickness grid. The spacer thickness was one of the unknowns since it varied as the steel plate was deformed under the applied force. Zero stress is registered when the plate is placed on a flat surface. The measured relative permeability as a function of the applied stress at the bottom of the plate are shown in FIG. 24. This illustrates the capability to measure stress (or strain) on a buried steel layer through relatively thick intermediate aluminum and insulating layers.

Figure 25:
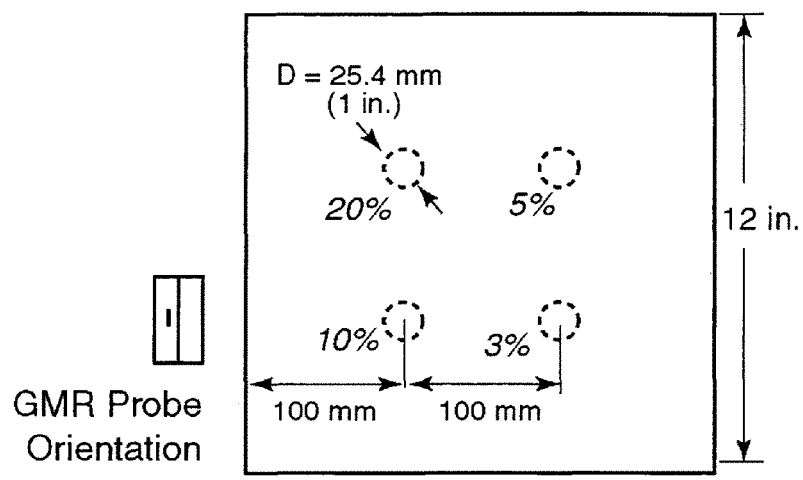
FIG. 25 shows the layout of a GMR sensor and 6.4 mm thick sample plate for simulating material loss.
Figure 26:
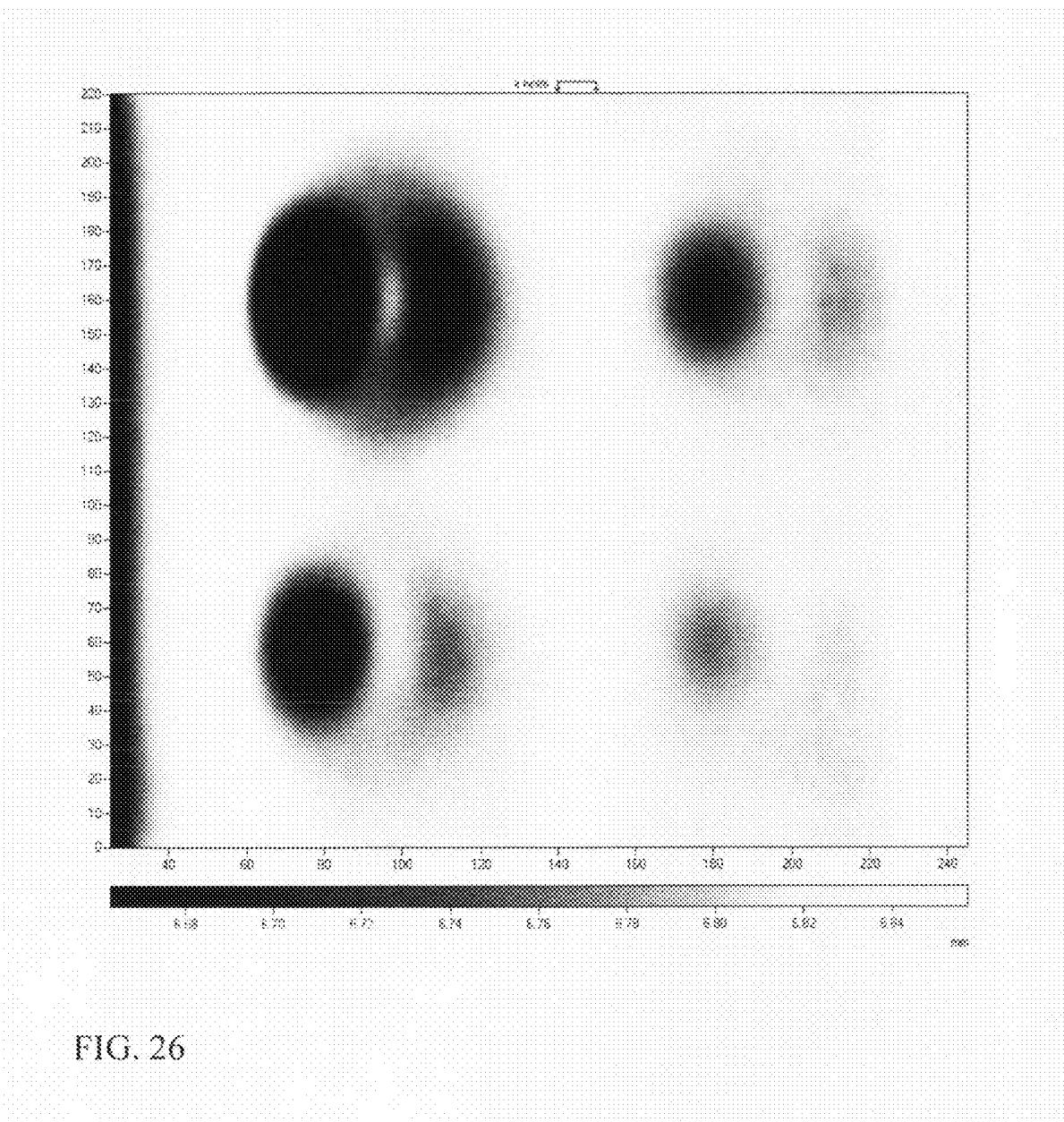
FIG. 26 shows an image of material loss in a 6.4 mm (0.25-in.) thick aluminum plate, generated with the GMR probe at 100 Hz. The four regions represent 3%, 5%, 10%, and 20% loss. Distances and thickness estimates are in millimeters.
Figure 27:
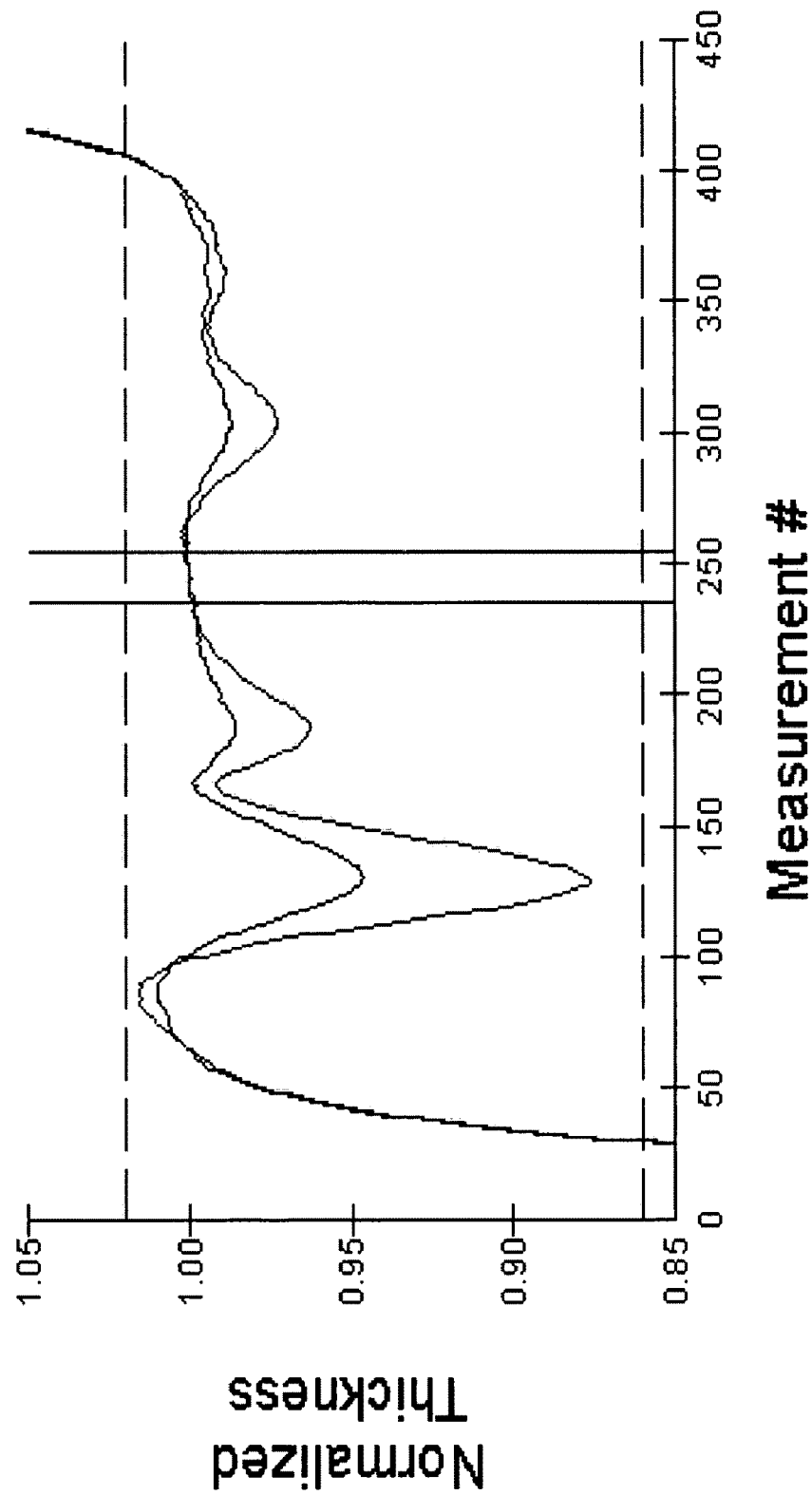
FIG. 27 shows the normalized thickness estimate for two lengthwise scans through the centers of the 10% and 3% regions, and the 20% and 5% regions.

GMR-based sensors can also be used to measure material loss of relatively thick parts. A representative sample is shown in FIG. 25. In this case, four flat-bottom circular areas were milled out of a 6.4 mm (0.25-in.) aluminum alloy plate. The depths of the four depressions, simulating material loss, are 3%, 5%, 10%, and 20%, respectively. Using the GMR probe and an excitation frequency of 100 Hz, the thickness scan image in FIG. 26 was generated. The orientation of the sensor probe is such that the primary windings lie along the vertical direction, with the secondary positioned in the left half-wavelength. The "double hump" signature produced by this sensor is apparent. The plot in FIG. 27 shows the normalized thickness estimate for two of the 220 individual lengthwise scans that comprise the area scan, through the centers of the 10% and 3% regions, and the 20% and 5% regions. The source of the "double-hump" response to what is a square pulse in thickness change, stems from the fact that the largest change to the signal is observed when the perturbation (e.g., thickness change) falls under a primary winding. The main lobe is generated by the response to the center winding, which carries twice the current and is closer to the secondary than the two outer winding legs. The second smaller lobe is the response to the outer (or return) primary winding on the opposite side of the secondary. It has the same polarity, because both the current direction and the relative position with respect to the secondary are reversed with respect to the center winding. The response to the third leg of the primary winding is weaker still and appears to the left of the main lobe. Its polarity is reversed because while the current flows in the opposite direction, it is on the same side of the secondary as the center winding.

The edge effect, i.e. when part of the sensor footprint is outside the sample area, is very prominent both in the plot and in the scan image. It is much more pronounced in the horizontal direction, because of the geometry of the probe, which is built to appear uniform (and in principle infinite) in the direction parallel to the longer drive winding segments. The edge effect is more prominent on the left side, since the secondary sensing element is closer to the left edge of the probe. The polarity of the edge effect is opposite on the two sides as described above. The vertical edge effect is not present in the scan image because the image was normalized by the thickness in the area between the 140- and 150-mm positions.

Figure 28:
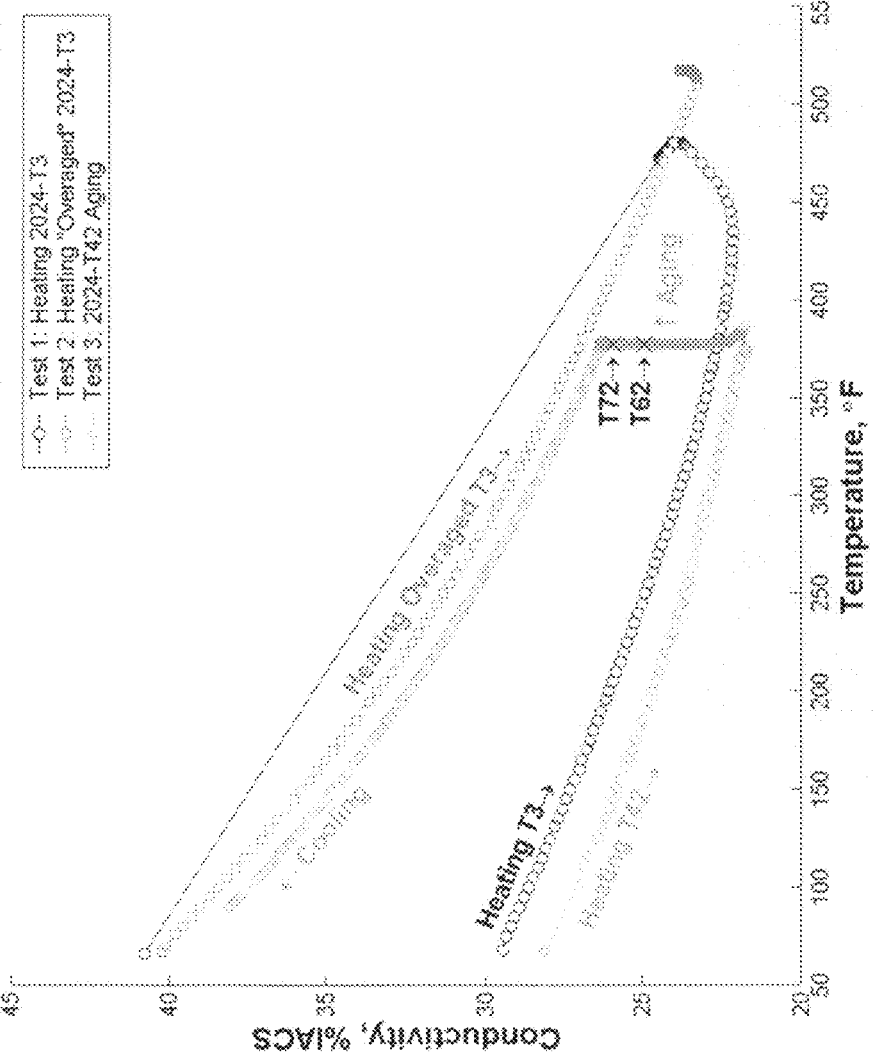
FIG. 28 shows the MWM measured conductivity changes for Al 2024 at temperatures up to 270° C.
Figure 29:
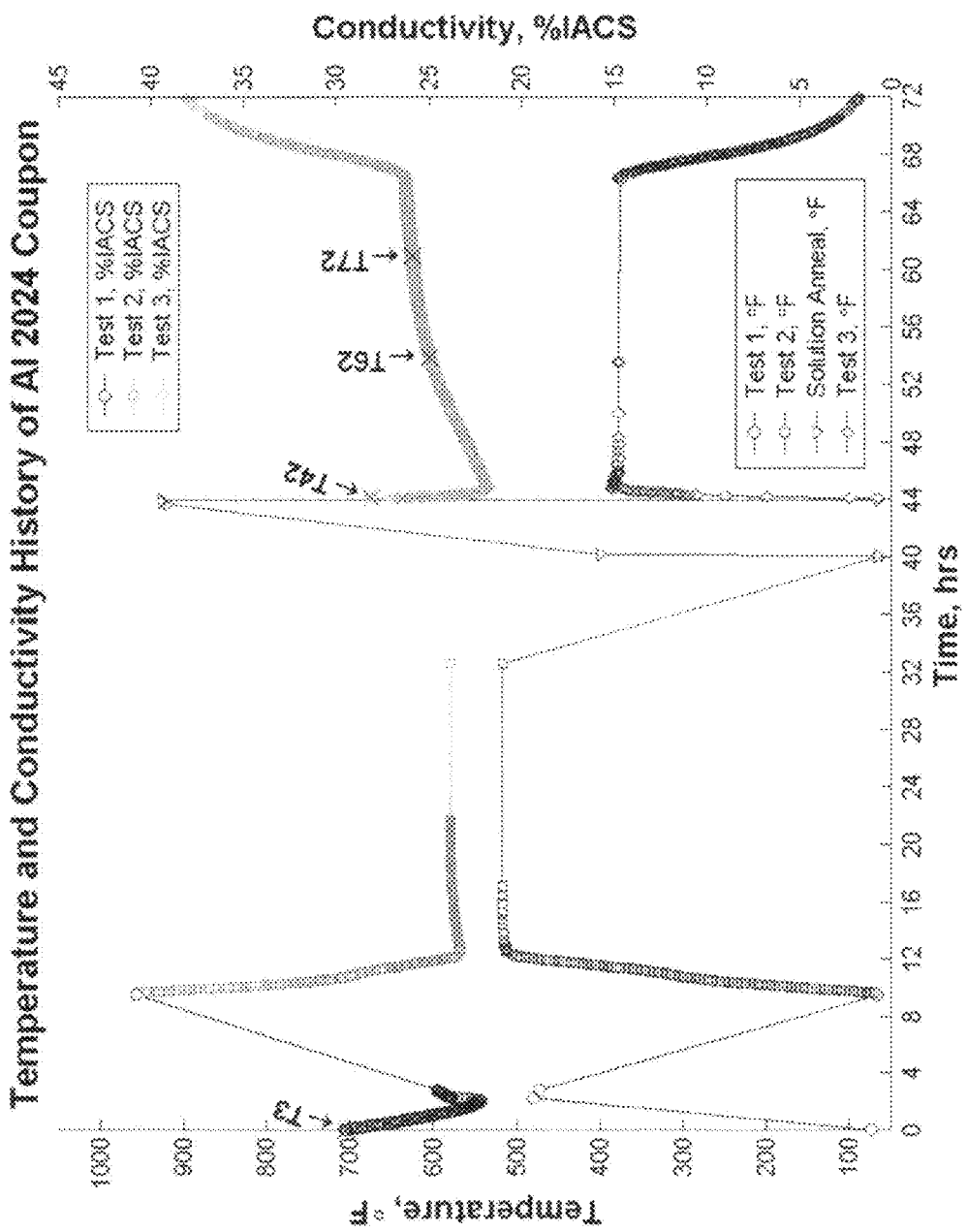
FIG. 29 shows the temperature and conductivity history for an Al 2024 coupon heat treatment.
Figure 30:
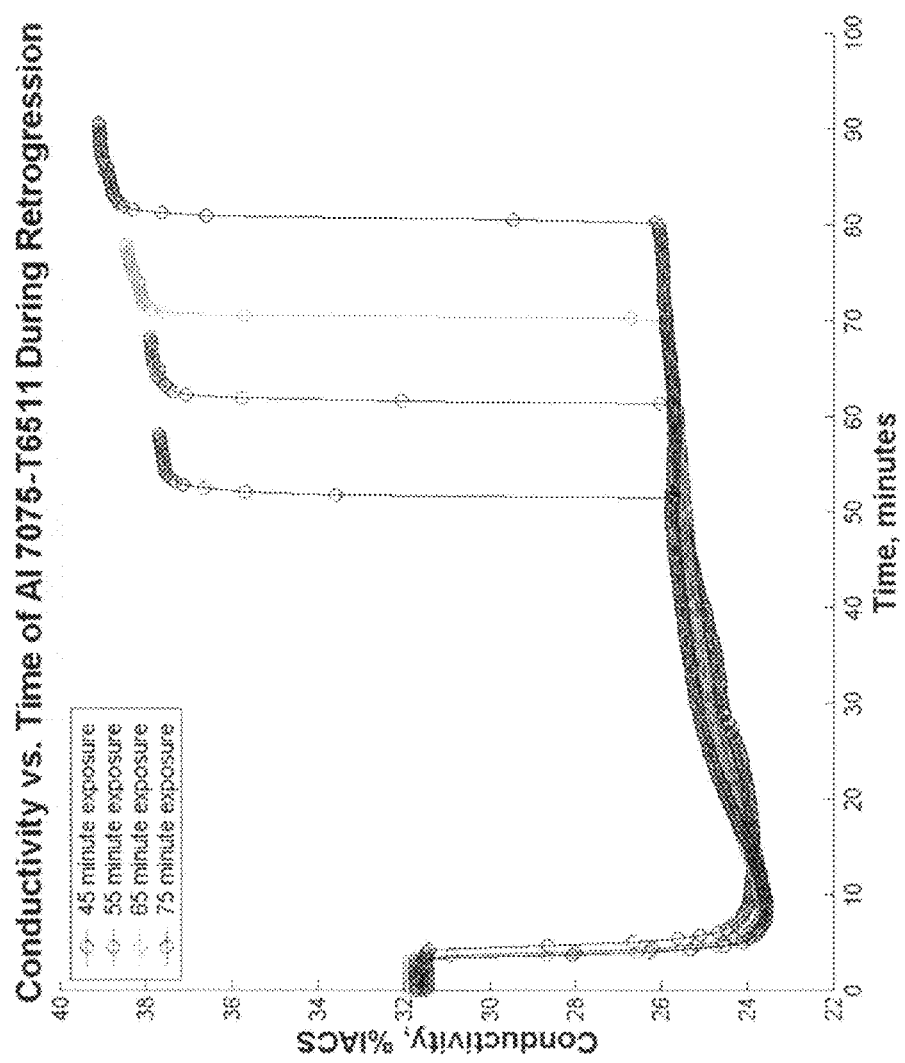
FIG. 30 shows the MWM measured conductivity transient of Al 7075 during retrogression.

The MWM sensors and sensor arrays can also be used to monitor heat treatment of metals and for monitoring high temperature tests on metals and alloys, metal processing and the condition of elevated temperature components. FIG. 28 shows the results of standard MWM configuration lift-off and conductivity measurements of an aluminum 2024 coupon during various heat treatments at temperatures up to 270° C. The plots shows conductivity versus temperature for an aluminum 2024 coupon as the original T3 condition was overaged and then reheated. Following a solution anneal to produce the T42 condition, the coupon was again heated to monitor conductivity changes as the T62, T72 and overaged conditions were achieved. These measurements used a single-channel MWM sensor constructed of copper conductors on a Kapton™ substrate. The sensors can also be fabricated onto ceramic substrates, such as alumina, for even higher temperature operation. Although not generally flexible, these ceramic substrate arrays can be molded into the shape of the test article. FIG. 29 shows the corresponding temperature and conductivity history, which illustrates the capability of the sensor to monitor the processing of the metal and the condition during the treatment. Similarly, FIG. 30 illustrates the alloy condition changes during retrogression. The conductivity drops dramatically after the coupon is placed in the furnace. Then, after dwelling at or exposing the coupon to an elevated temperature such as 400° F. the coupon is quenched. This results in a higher electrical conductivity than was present initially, with the effect depending on the exposure duration.

Figure 31:
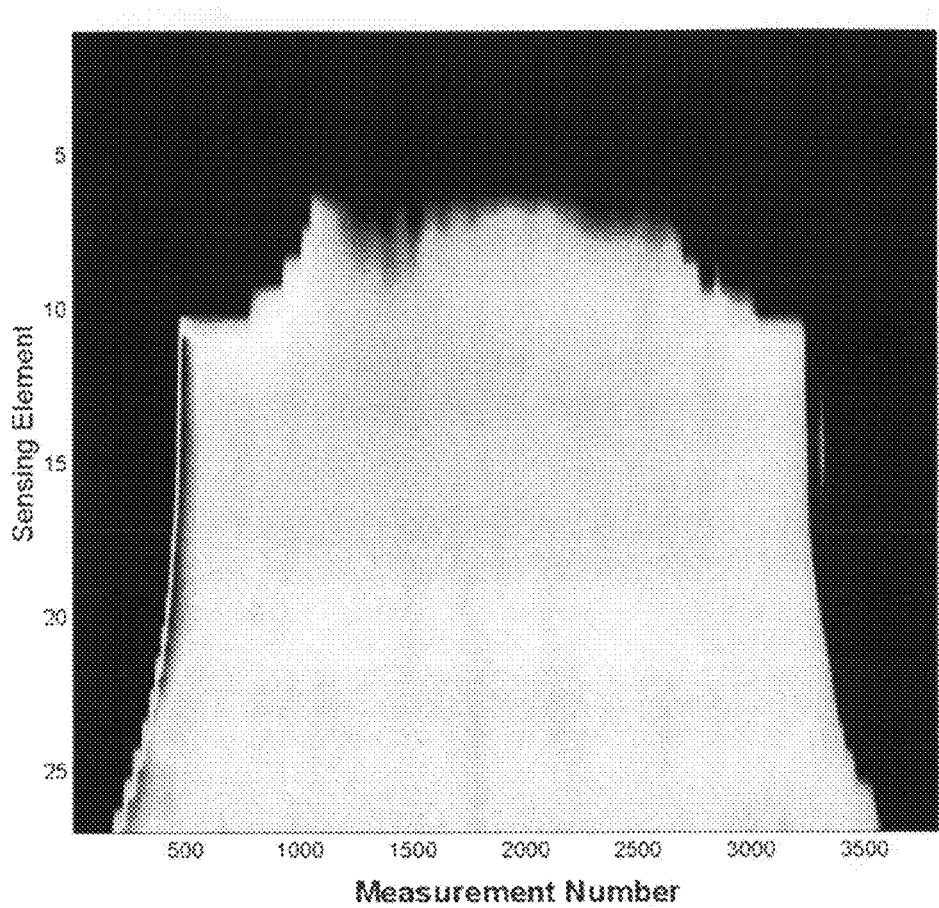
FIG. 31 shows a normalized permeability image obtained from an MWM-Array scanned over a double-notched 4340 low-alloy steel tensile specimen after failure in a tension test, with an excitation frequency of 1 MHz and the extended portions of the primary winding oriented parallel to the loading axis.
Figure 32:
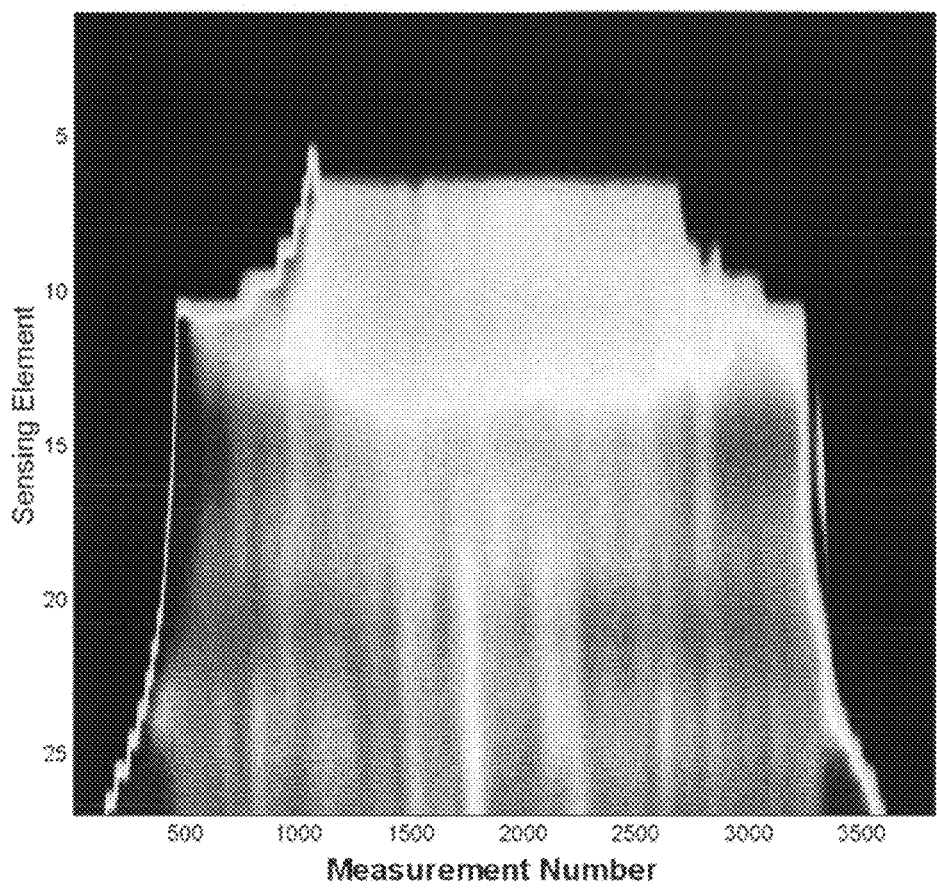
FIG. 32 shows a normalized permeability image obtained from an MWM-Array scanned over a double-notched 4340 low-alloy steel tensile specimen after failure in a tension test, with an excitation frequency of 158 kHz and the extended portions of the primary winding oriented parallel to the loading axis.
Figure 33:
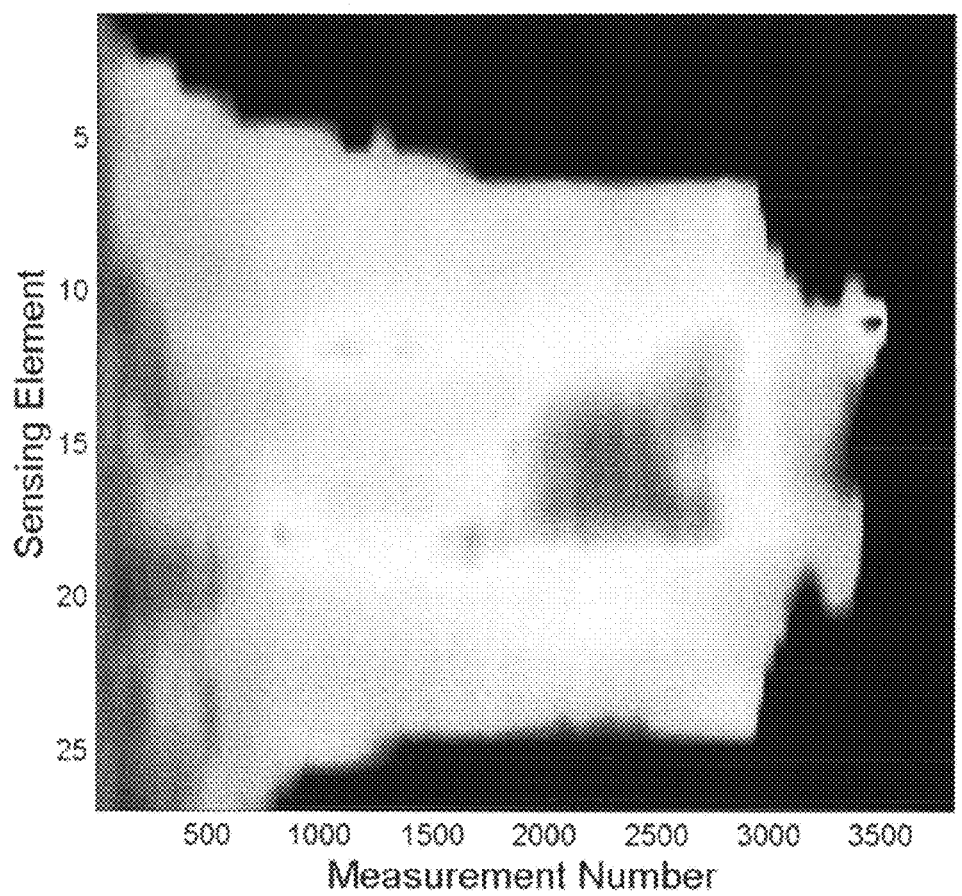
FIG. 33 shows a normalized permeability image obtained from an MWM-Array scanned over a double-notched 4340 low-alloy steel tensile specimen after failure in a tension test, with an excitation frequency of 1 MHz and the extended portions of the primary winding oriented perpendicular to the loading axis.

MWM-Arrays also provide a capability to perform bi-directional magnetic permeability measurements in a scanning mode. FIG. 31 through FIG. 33 provide images of the magnetic permeability for a broken tensile specimen of 4340 low alloy steel. The MWM-Array was scanned across and along the gage section of a specimen broken in a tensile test and the permeability was measured at two frequencies, 158 kHz for FIG. 32 and 1 MHz for FIG. 31 and FIG. 33. In FIG. 31 and FIG. 32 the extended portions of the primary winding were oriented parallel to the loading axis. In FIG. 33 the extended portions of the primary winding were oriented perpendicular to the loading axis. This illustrates the potential to map residual stress variations produced in parts fabricated from carbon and low alloy steels, for example by a hard landing in the latter case. Notice that the permeability images at low and high frequencies reveal stress changes with distance from the surface. A high residual stress region near the fracture is indicated in the images of FIG. 33. To create these images, a permeability/lift-off measurement grid was used, assuming a known conductivity and an infinite half-space (i.e., the steel layer is assumed to be infinitely thick). Since the lift-off or distance between the sensing windings and the test material is being measured through the measurement grids, the residual stress measurement can be performed in a non-contact mode, which ensures that the sensor and probe assembly do not influence the stress distribution on the component.

These eddy current sensors and sensor arrays permit the measurement and monitoring of stresses (applied and residual) in steel components. The sensors can be used to inspect selected locations on a part by placing the sensor over the area of interest, scanning over the area, or permanently mounting or affixing the sensor to the surface. By measuring with multiple sensor orientations, the permeability and stress distribution can be inferred. Preferably, the orientations are perpendicular to one another so that the biaxial stress distribution is obtained. The anisotropy is most easily obtained when the orientation of the sensor or sensor array has the direction of greatest sensitivity aligned with the directions of the maximum and minimum principal stresses in the materials. When the sensors are flexible and can conform to the complex geometry surfaces, the sensors can be supported by a bottom foam support that makes the sensor essentially flat until placed onto the surface. Alternatively, the sensors can be molded into a fixture that conforms to or has a shape similar to the geometry of the test material.

These same techniques can be used to detect and characterize overload effects on components. As examples, excessive mechanical or thermal loading on a component can compromise the structural integrity of a component so that it fails during subsequent use. In magnetizable materials such as most steels, patterns of the magnetic permeability distribution over the surface of critical components can reflect these overload conditions. The permeability can be measured using single element eddy current sensors placed at selected locations and in different orientations, eddy current sensor arrays permanently mounted at selected locations in different orientations, and by imaging sensors, such as MWM-Arrays, scanned in different orientations.

The capability to monitor applied and residual stress on a component also permits other properties to be inferred, such as the weight of an article. For example, the weight of an aircraft or changes in the weight in the aircraft can be inferred from magnetic permeability measurement performed on steel landing gear components. Eddy current sensor arrays can be scanned or mounted at selected locations that reflect the load transfer from the weight of the aircraft about the landing gear. The arrays should be mounted or scanned in the orientation parallel to the direction of maximum principal stresses. Other orientations could also be included to provide a more complete observation of the stress distribution.

Combinations of permanently mounted and scanning sensors and sensor arrays can be used to image and monitor stress distributions on simple and complex surfaces. The surfaces can be flat or non-flat geometry and may be on layered materials, such as lap joints. Measurements can also be performed in contact or non-contact modes, with parts of the sensor mounted on an opposing surface.

These can be in the form of layers, gradient materials with properties varying with depth or near critical features such as holes, fibers or coated fibers, weld material or entire components such as a fitting, bolt, or joint. State-sensitive materials can also be used in the design and use of critical components. These materials can be ones whose magnetic permeability, dielectric permittivity, or electrical conductivity varies with stress, temperature, thermal or mechanical overload, fatigue damage, crack presence, or some combination of these effects. The materials would be selected for use with a particular component based on the sensitivity of the materials and the properties of the component. For example, Table 1 listed several materials suitable for an eddy current sensor but these same materials would not be suitable for a dielectric sensor.

Figure 34:
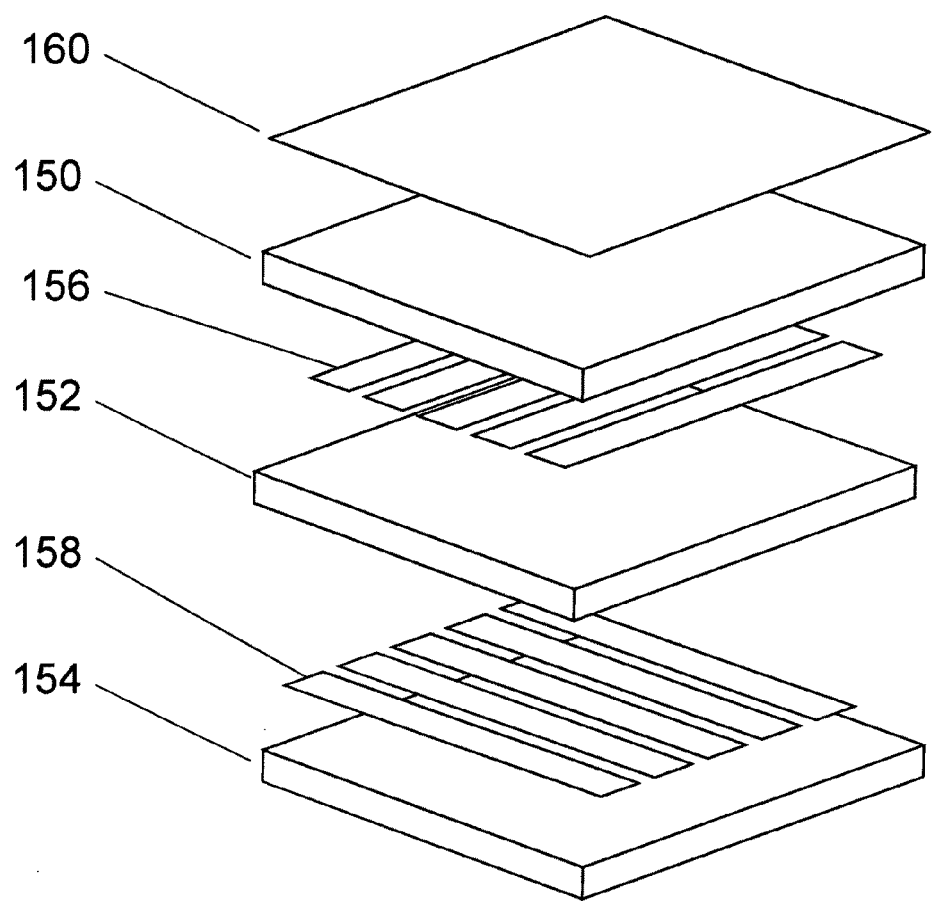
FIG. 34 shows an illustration of segments of state-sensitive material embedded between layers of a test article.

These state-sensitive materials could be placed on the surface or embedded between material layers of the test component. FIG. 34 shows a sensor 160 above the top layer 150, middle layer 152, and bottom layer 154 of a three layer component. State-sensitive materials are embedded between the top and middle layers 156 and between the middle and bottom layers 158. For monitoring stress or fatigue, the state-sensitive layers can contain laminates of multiple strips or some other pattern that has different orientations at the different depths in the material. When the properties of the layers (156 and 158) are measured, the pattern for the effective property (e.g., permeability) will change depending upon the state (e.g., stress) on the component. This can also be applied to the monitoring of stress around fasteners, as described in U.S. patent application Ser. No. 10/351,978.

In a similar fashion, eddy current sensors can be mounted between layers to measure fatigue damage and stresses or for detection of cracks. This can also include placing the electrical conductors for the drive and sense windings on different layers of the component as well. The sensors themselves can also be supported with durable substrates, such as stainless steel or ceramic to prevent damage to the sensor conductors. The sensors may even be embedded within these durable supports. In one embodiment one or two sets of drive winding with or without a magnetic substrate and with or without a protective coating to limit fretting damage are embedded between layers with or without an embedded array of sensing elements. An array of sense elements is then scanned across the outer surface to measure the field. This increases sensitivity to cracks or stress changes between the layers because the applied field does not have to diffuse through the metal and then back again when compared to a non embedded drive, scanning method. In another embodiment with one embedded sensor or sensitive material, protective layers are used to limit fretting damage at the faxing surface.

Figure 35:
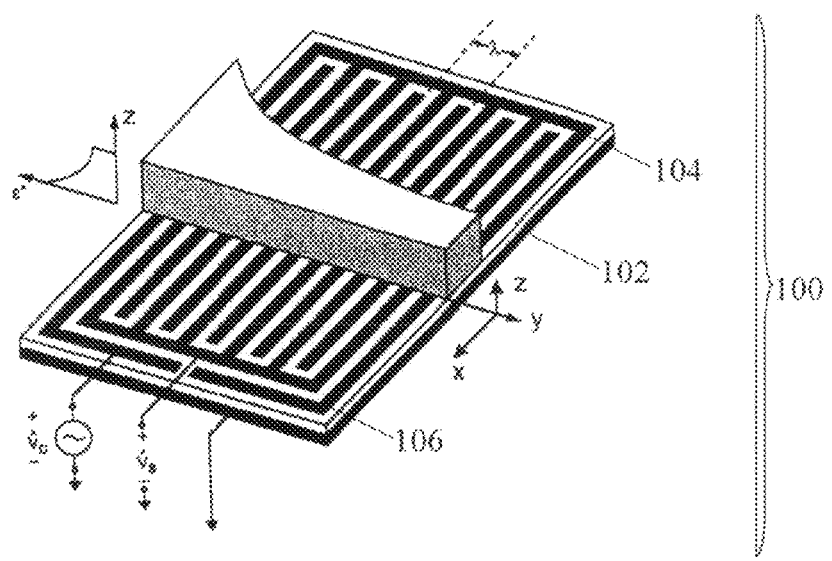
FIG. 35 is a representative single wavelength interdigitated electrode dielectrometer with spatially periodic driven and sensing electrodes of wavelength λ that can measure dielectric properties of the adjacent material.

A variety of sensors can be used to measure the response of the state sensitive materials. For example, for insulating or weakly conducting materials such as fiberglass composites, capacitive or dielectric sensors can be used. The sensors are the electromagnetic dual to the inductive sensors, with electric fields taking the place of magnetic fields for inspecting the materials. A representative single sided sensor geometry is shown in FIG. 35. The application of a sinusoidally varying potential of complex magnitude v and angular frequency $\omega=2\pi f$ results in the flow of a terminal current with complex amplitude I, whose magnitude and phase are dependent on the complex permittivity of the material. The capacitive sensor 100 in one preferred embodiment has interdigitated electrodes as presented in U.S. Pat. Nos. 4,814,690 and 6,380,747 and in U.S. patent application Ser. No. 10/040,797, filed Jan. 7, 2002, and Ser. Nos. 10/225,406, filed Aug. 20, 2002, the entire teachings of which are hereby incorporated by reference. This sensor 102 utilizes a pair of interdigitated electrodes 104 and 106 to produce a spatially periodic electric field. The electrodes are adjacent to the material of interest with an insulating substrate and a ground plane on the other side of the substrate. One of the two electrodes, 104, is driven with a sinusoidally varying voltage, $v_D$, while the other, 106, is connected to a high-impedance buffer used to measure the magnitude and phase of the floating potential, $v_S$. The periodicity of the electrode structure is denoted by the spatial wavelength $\lambda=2\pi/k$, where k is the wavenumber.

In another embodiment sensor diagnostics and/or recalibration is performed for individual surface mounted or embedded sensors or networks of sensors by performing an act or exposing the sensor to a condition change that changes one or more unknowns while not changing at least one other unknown (e.g., lift-off). In one such method the temperature is varied using a heat source or measurements are made at different ambient temperatures. This changes conductivity and or permeability with lift-off constant. In another such method, stress (or external load) is altered to again vary conductivity or permeability of the MUT or added sensitive material with lift-off and layer thicknesses constant. In another embodiment another layer is added keeping all else constant. In another embodiment the scanning of a drive or sense array relative to an embedded drive or sense array is accomplished at different lift-offs, temperatures or applied stresses. In still another method a bias field is used to change the permeability, including directional variations if practical. Both for performance check and measurement enhancements. The sensor performance is verified by comparing to expected behavior. Recalibration is performed relative to expected results by monitoring temperature or stress with thermostats/thermocouples or strain gages or some other means or model prediction relative to load/source of change.

While the embodiments of the invention have been particularly shown and described with reference to preferred embodiments thereof, it will be understood to those skilled in the art that various changes in form and details may be made therein without departing from the spirit and scope of the embodiment of the invention as defined by the appended claims.

REFERENCES INCORPORATED BY REFERENCE IN THEIR ENTIRETY

Auld, B. A. and Moulder, J. C. (1999), "Review of Advances in Quantitative Eddy-Current Nondestructive Evaluation," Journal of Nondestructive Evaluation, vol. 18, No. 1.

Bozorth, R. M., Ferromagnetism, IEEE Press, 1978.

Bray, D. E., ed., Residual Stress Measurement and General Nondestructive Evaluation, PVP-Vol. 429, ASME Pressure Vessels and Piping Conference, Atlanta, Ga., ASME, 2001.

Grendahl, S. and R. Kilbane (2002), "Environmentally Assisted Cracking Concerns for Cadmium Replacement," presented at Tri-Service Corrosion Conference, 2002.

Hydrogen in Metals, Proceedings of the Second Japan Institute of Metals, International Symposium, 1979.

Interrante, C. and Pressouyre, G. "Current Solutions to Hydrogen Problems in Steels," Proceedings of the First International Conference, ASM, 1982.

Lawrence, S. C. "Hydrogen Detection Gage," Hydrogen Embrittlement Testing, ASTM STP 543, 1974, pp. 83-105.

The following references are also incorporated herein by reference in their entirety.

1. DOE Phase II Proposal, titled "Intelligent Probes for Enhanced Non-Destructive Determination of Degradation in Hot-Gas-Path Components," Topic #44c, dated March 23, 2002.
2. Air Force Phase II Proposal, titled "Detection and Imaging of Damage, Including Hydrogen Embrittlement Effects in Landing Gear and Other High-Strength Steel Components," Topic #AF01-308, dated April 9, 2002.
3. NASA Phase II Proposal, titled "Shaped Field Giant Magnetoresisitive Sensor Arrays for Materials Testing," Topic #01-II A1.05-8767, dated May 2, 2002
4. Navy Phase I Proposal, titled "Observability Enhancement and Uncertainty Mitigation for Engine Rotating Component PHM," Topic #N02-188, dated August 14, 2002.
5. Final Report submitted to NASA, titled "Shaped Field Giant Magnetoresisitive Sensor Arrays for Materials Testing," dated May 3, 2002.
6. Final Report submitted to Air Force, titled "Detection and Imaging of Damage, Including Hydrogen Embrittlement Effects in Landing Gear and Other High-Strength Steel Components," dated July 3, 2002.
7. Technical Report titled "MWM Examination of Twenty X2M Steel Fatigue Specimens After Abusive Grinding," US ARMY Final Report 08162002.
8. Technical paper titled "Friction Stir Weld Inspection through Conductivity Imaging using Shaped Field MWM® -Arrays," Proceedings of the 6$^{th}$ International Conference on Trends in Welding, Callaway Gardens, GA; ASM International, January 2003.
9. Technical paper titled "MWM Eddy Current Sensor Array Imaging and Hidden Corrosion for Improved Fleet Readiness and Cost Avoidance," of Surface presented at U.S. Army Corrosion Conference, Clearwater Beach; FL, February11-13, 2003.
10. Technical paper titled "Remote Temperature and Stress Monitoring Using Low Frequency Inductive Sensing," SPIE NDE/Health Monitoring of Aerospace Materials and Composites, San Diego, CA, March 2-6, 2003.
11. Technical paper titled "In-Situ Crack Detection and Depth Discrimination for Coated Turbine Blade Contact Faces," presented at ASNT Spring Conference, Orlando, Florida, March 10-14, 2003.
12. Technical paper titled "MWM Eddy Current Sensor Array Characterization of Aging Structures Including Hidden Damage Imaging," presented at the NACE Conference, San Diego; CA, March 17-19, 2003.
13. Technical paper titled "Material Condition Monitoring Using Embedded and Scanning Sensors for Prognostics," presentation at the 57$^{th}$ MFPT Conference, Virginia Beach, VA; April 2003.
14. Technical paper titled "Nondestructive Evaluation for CBM and PHM of Legacy and New Platforms," 57$^{th}$ MFPT Conference, Virginia Beach, VA; April 2003.
15. Technical paper titled "Validation of Multi-Frequency Eddy Current MWM Sensors and MWM-Arrays for Coating Production Quality and Refurbishment Assessment," submitted for the proceedings of the ASME/IGTI Turbo conference, June 2003, Atlanta, GA.
16. Technical paper titled "Corrosion Detection and Prioritization Using Scanning and Permanently Mounted MWM Eddy-Current Arrays", Tri-Service Corrosion Conference, January 2002.
17. Technical paper titled "Surface Mounted and Scanning Periodic Field Eddy-Current Sensors for Structural Health Monitoring," presented at IEEE Aerospace Conference: Prognostics & Health Management for Aging Aircraft; March 2002.
18. Technical paper titled "MWM-Array Characterization and Imaging of Combustion Turbine Components," presented at EPRI International Conference on Advances in Life Assessment and Optimization of Fossil Power Plants, Orlando, FL; March 2002.

-continued

19. Technical paper titled "Corrosion Detection and Prioritization Using Scanning and Permanently Mountable MWM Eddy-Current Arrays," presented at U.S. Army Corrosion Summit, March 2002.
20. Technical paper titled "MWM-Array Characterization and Imaging of combustion Turbine Components," presented at EPRI International Conference on Advances in Life Assessment and Optimization of Fossil Fuel Power Plants, March 2002.
21. Technical paper titled "Application of MWM Sensors and MWM-Arrays for Inspection of Aircraft Components," presented at NAVAIR NDT Working Group, April 2002.
22. Technical paper titled "Application of MWM® Eddy- Current Technology during Production of Coated Gas Turbine Components," presented at 11 to International Symposium on Nondestructive Characterization of Materials, Berlin, Germany; June 2002.
23. Technical paper titled "High Temperature Eddy-Current Sensors for Heat Treatment Monitoring," presented at AeroMat, June 2002.
24. Technical paper titled "Eddy-Current Array Volumetric Imaging of Microstructure and Flaws for Thick Components," presented at AeroMat, June 2002.
25. Technical paper titled "Absolute Electrical Property Imaging using High Resolution Inductive, Magnetoresistive and Capacitive Sensor Arrays for Materials Characterization," presented at 11 to International Symposium on Nondestructive Characterization of Materials, Berlin, Germany; June, 2002.
26. Technical paper titled "Friction Stir Weld Inspection for Lack of Penetration Defects via Conductivity Mapping using MWM Eddy Current Sensor Arrays," presented at AeroMat, June 2002.
27. Technical paper titled "Eddy Current Sensor Technology for Real-Time State Monitoring, Condition Based Maintenance, and Life Management," presented at ONR Prognostics Workshop, July 2002.
28. Technical paper titled "MWM-Array Eddy Current Sensors for Detection of Cracks in Regions with Fretting Damage," published in ASNT Materials Evaluation, Volume 60, No. 7, pp 870-877; July 2002.
29. Technical paper titled "Residual and Applied Stress Estimation from Directional Magnetic Permeability Measurements with MWM Sensors," published in ASME Journal of Pressure Vessel Technology, Volume 124, pp 375-381; August 2002.
30. Technical paper titled "Rapid High-Resolution Corrosion Imaging and Detection with MWM Eddy Current Arrays," presented at $5^{th}$ International Aircraft Corrosion Conference, August 2002.
31. Technical paper titled "High-Resolution, Deep Penetration and Rapid GMR/Eddy Current Array Imaging of Weld Condition and Quality" presented at ASNT Structural Materials Technology - NDE/NDT for Highways and Bridges, September 2002.
32. Technical paper titled "High Resolution MWM-Array Imaging of Cracks in Fretting Regions of Engine Disk Slots," presented at the 6th Joint FAA/DoD/NASA Aging Aircraft Conference, September, 2002.
33. Technical paper titled "Multi-Site Damage Imaging of 3rd Layer Cracks in Lap Joints using MWM-Arrays," presented at the 6th Joint FAA/DoD/NASA Aging Aircraft Conference, September, 2002.
34. Technical paper titled "Conformable Eddy-Current Sensors and Arrays for Fleet-wide Gas Turbine Component Quality Assessment," published in ASME Journal of Engineering for Gas Turbines and Power, Volume 124, No. 4, pp 904-909; October 2002.
35. Technical paper titled "MWM-Array Eddy Current Testing for Corrosion and Fatigue Damage," presented at Air Transport Association, October 2002.
36. Technical paper titled "Characterization and Imaging of Coated Turbine Components with MWM Sensors and MWM-Arrays," presented at ASM Heat Treat/Surface Engineering, October 2002.
37. Technical paper titled "Thin, Conformable Eddy Current Sensor Arrays for Difficult-to-Access Location Inspections," presented at Defense Working Group, November 2002.
38. Technical paper titled "Health Monitoring for Landing Gear and Other Critical Components," presented at ASIP 2002, December, 2002.
39. Technical paper titled "MWM-Eddy-Current Arrays for Crack Initiation and Growth Monitoring," submitted to International Journal of Fatigue, from the International Conference on Fatigue Damage of Structural Materials IV, Hyannis, MA, 2002.

What is claimed is:

1. A method for inspection of magnetizable materials, said method comprising:
    disposing a sensor having at least two parallel drive conductors and at least one sense element proximate to a surface of a test material at more than one location;
    passing a time-varying electric current through the drive conductor to create a magnetic field; and
    measuring a response from each sense element to determine magnetic permeability correlated with an overload effect, the overload effect being an area having a low residual stress relative to a background residual stress of the test material.
2. The method as claimed in claim 1 wherein the response is the permeability distribution over the material surface.
3. The method as claimed in claim 1 wherein the at least one sense element comprises a plurality of sense elements.
4. The method as claimed in claim 3 wherein the sensor is mounted to the surface of the material at a fatigue critical area.
5. The method as claimed in claim 4 wherein the sensor is a first sensor, the method further comprising mounting at least one additional sensor in a different orientation than the first sensor.
6. The method as claimed in claim 3 wherein the measuring comprises scanning the sensor over the surface of the test material at at least two different orientations.
7. The method as claimed in claim 1 wherein the test material is a landing gear of an aircraft.
8. The method of claim 7, wherein the landing gear comprises steel.
9. The method of claim 7, wherein disposing the sensor comprises permanently mounting the sensor on the landing gear.
10. The method of claim 1, wherein the time-varying electric current comprises a direct current (DC) offset.
11. The method of claim 1, further comprising estimating a weight or a change in weight of an aircraft from the determined magnetic permeability.
12. The method of claim 1, wherein the sensor is a first sensor, the method further comprising scanning at least one additional sensor having a different orientation than the first sensor.
13. The method of claim 1, further comprising identifying a region of residual stress relaxation based on the determined magnetic permeability.
14. The method of claim 1, further including correlating the determined magnetic permeability with the overload effect.
15. A method for inspection of magnetizable materials, said method comprising:
    disposing a sensor having a plurality of sense elements proximate to a surface of a test material;
    passing a time-varying electric current having a direct current (DC) offset through the drive conductor; and
    measuring a response from each of the plurality of sense elements to determine magnetic permeability correlated with an area of a low residual stress relative to a material background residual stress.
16. The method of claim 15, wherein the test material is a landing gear of an aircraft.
17. The method of claim 15, wherein the sensor comprises at least two parallel drive conductors.
18. The method of claim 15, further including correlating the determined magnetic permeability with the area of a low residual stress relative to a material background residual stress.

* * * * *